(12) United States Patent
Krause et al.

(10) Patent No.: US 6,701,174 B1
(45) Date of Patent: Mar. 2, 2004

(54) COMPUTER-AIDED BONE DISTRACTION

(75) Inventors: Norman Krause, Pittsburgh, PA (US); Robert W. Mendicino, Pittsburgh, PA (US); Kenji Shimada, Pittsburgh, PA (US); Lee Weiss, Pittsburgh, PA (US); Takeo Kanade, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 09/545,685

(22) Filed: Apr. 7, 2000

(51) Int. Cl.[7] .............................................. A61B 5/055
(52) U.S. Cl. ..................... 600/407; 600/425; 600/429; 382/128; 382/131; 382/132; 378/98.12; 378/21; 378/62; 378/63; 606/91
(58) Field of Search ............................... 382/128, 131, 382/132, 190, 199, 285, 203; 128/849, 920, 922; 600/407, 425, 429; 606/91; 378/98.12, 62, 63, 21

(56) References Cited

U.S. PATENT DOCUMENTS

| | | |
|---|---|---|
| 5,251,127 A | 10/1993 | Raab |
| 5,279,309 A | 1/1994 | Taylor et al. |
| 5,526,812 A | 6/1996 | Dumoulin et al. ........ 128/653.1 |
| 5,740,802 A | 4/1998 | Nafis et al. ............... 128/653.1 |

(List continued on next page.)

OTHER PUBLICATIONS

Delorme S. et al. "Three dimensional modeling and rendering of the human skeletal trunk from 2D radiographic images" 3–D Digital Imaging and Modeling. 1999. Proceedings Second International Conference on Ottawa, Ont., Canada Oct. 4–8, 1999, Los Alamitos, CA, USA, *IEEE Comput. Soc.*, US, pp. 497–505.

(List continued on next page.)

*Primary Examiner*—Marvin M. Lateef
*Assistant Examiner*—Jeoyuh Lin
(74) *Attorney, Agent, or Firm*—Kevin A. Oliver; Foley Hoag LLP

(57) ABSTRACT

A computer assisted orthopedic surgery planner software for generation of 3D (three dimensional) solid bone models from two or more 2D (two dimensional) X-ray images of a patient's bone. The computer assisted orthopedic surgery planner software reconstructs the bone contours by starting with a 3D template bone and deforming the 3D template bone to substantially match the geometry of the patient's bone. A surgical planner and simulator module of the computer assisted orthopedic surgery planner software generates a simulated surgery plan showing the animation of the bone distraction process, the type and the size of the fixator frame to be mounted on the patient's bone, the frame mounting plan, the osteotomy/coricotomy site location and the day-by-day length adjustment schedule for each fixator strut. All bone models and surgery plans are shown as 3D graphics on a computer screen to provide realistic, pre-surgery guidance to the surgeon. Post-operative surgical data may be fed back into the computer assisted orthopedic surgery planner software to revise the earlier specified one distraction trajectory in view of any discrepancy between the pre-operative plan data and the actual, post-operative data. Assistance in planning and carrying out a bone distraction surgery may be provided to remotely-located surgeons via the Internet using the computer assisted orthopedic surgery planner software at the service provider's location to generate specific surgical plans and simulation models for each surgeon requesting assistance. A physician-friendly 3D modeling approach in the computer assisted/orthopedic surgery planner software according to the present invention reduces the complexities and costs associated with a bone distraction surgery and thus allows more surgeons to practice bone distraction, thereby benefitting more patients in need of bone distraction.

20 Claims, 10 Drawing Sheets

U.S. PATENT DOCUMENTS

| | | | |
|---|---|---|---|
| 5,749,362 A | 5/1998 | Funda et al. | 128/653.1 |
| 5,765,561 A | 6/1998 | Chen et al. | |
| 5,769,092 A | 6/1998 | Williamson, Jr. | 128/898 |
| 5,799,055 A | 8/1998 | Peshkin et al. | 378/42 |
| 5,806,518 A | 9/1998 | Mittelstadt | 128/653.1 |
| 5,824,085 A | 10/1998 | Sahay et al. | 623/16 |
| 5,871,018 A | 2/1999 | Delp et al. | 128/898 |
| 5,880,976 A | 3/1999 | DiGioia III et al. | |
| 5,970,499 A | 10/1999 | Smith et al. | |
| 5,995,738 A | 11/1999 | DiGioia, III et al. | 395/500.32 |
| 6,100,862 A | 8/2000 | Sullivan | |

OTHER PUBLICATIONS

Zdravkovic V et al. "Computer–Assisted Preoperative Planning (CAPP) in Orthopaedic Surgery," *Computer Methods and Programs in Biomedicine*, Elsevier, Amsterdam, NL, 32(2): Jun. 1990, pp. 141–146.

Boljevic Z et al. "Computer–Assisted Three–Dimensional Modeling for Definition and Correction of Deformities in Orthopaedic Surgery," *Proceedings of the International Conference on Information Technology Interfaces*, pp. 357–364, 1993.

Partial International Search Report, PCT Application Serial No. PCT/US 01/11272, Feb. 27, 2002.

Hong, Lin, et al., "The Cross–Sectional Image Guided Ilizanov Frame Positioning for the Surgery Planning of Lower Extremely Deformity Correction", Proceedings—19$^{th}$ International Conference IEEE/MBS, Oct. 30, 1997; Nov. 2, 1997, p. 767–769, Chicago, IL, USA.

Myoung–Hee Kim, et al., "Telediagnosis System for Orthopedic Deformity Analysis Based on 3D Medical Imaging", Proceeding of SPIE, vol. 3976, Feb. 13–15, 2000, p. 324–333, Seoul, Korea.

Cherkashin, A.M., et al., "Interactive Ilizarov Database: An Electronic Patient Record for Orthopaedics", Proceedings. Towards an Electronic Patient Record '96, Twelfth International Symposium on the Creation of Electronic Health Record System and Global Conference on Patient Cards, San Diego, CA, USA, vol. 2, May, 13–18, 1996, p. 293–295, Newton, MA, USA.

Vilijam Zdravkovic and Ranko Bilic, "Computer–assisted preoperative planning (CAPP) in orthopaedic surgery", Computer Methods and Programs in Biomedicine, 32 (1990), pp. 141–146, COMMET 01093, Elsevier Science Publishers B.V. (Biomedical Division).

D. Paley, H. F. Kovelman, and J.E. Herzenberg, "Ilizarov Technology", Advances in Operative Orthopaedics, vol. 1, Mosby Year Book, Inc., 1993, pp. 243–287.

Sabine Coquillart, "Extended Free–Form Deformation: A Sculpturing Tool for 3D Geometric Modeling", Computer Graphics, vol. 24, No. 4, Aug. 1990, pp. 187–196.

T. Sederberg and S. Parry, "Free–Form Deformation of Solid Geometric Models", presented at SIGGRAPH '86 Proceedings, Dallas, Texas (1986), vol. 20, No. 4, pp. 151–160.

S. Coquillart, "Extended Free–Form Deformation: A Sculpturing Tool for 3D Geometric Modeling", INRIA, Recherche, No. 1250, Programme 6, France (Jun. 1990), pp. 1–18.

A. H. Barr, "Global and Local Deformations of Solid Primitives", Computer Graphics, vol. 18, No. 3, Jul. 1984, pp. 21–31.

Beom–Seok Shin and Yeong Gil Shin, "Fast 3D Solid Model Reconstruction From Orthographic Views", Computer–Aided Design, vol. 30, No. 1, 1998, pp. 63–76.

C. Lawrence, J. Zhou, and A. Tits, "User's Guide for CFSQP Version 2.3: A C Mode for Solving (Large Scale) Constrained Nonlinear (Minimax) Optimization Problems, Generating Iterates Satisfying All Inequality Constraints", published by the Electrical Engineering Department and the Institute for Systems Research, University of Maryland, College Park, Maryland 20742 (1995), pp. 1–69.

M. R. Stytz, G. Frieder, and O. Frieder, "Three–Dimensional Medical Imaging: Algorithms and Computer Systems", ACM Computing Surveys, vol. 23, No. 4, Dec. 1991, pp. 421–499.

Hiroshi Masuda and Masayuki Numao, "A Cell–Based Approach for Generating Solid Objects from Orthographic Projections", a Research Report published by IBM Research, Tokyo Research Laboratory, IBM Japan, Ltd., on Nov. 13, 1995, pp. 1–29.

Qing–Wen Yan, C L Philip Chen, and Zesheng Tang, "Efficient Algorithm for the Reconstruction of 3D Objects from Orthographic Projections", Computer–Aided Design, vol. 26, No. 9, Sep. 1994.

H. Lin, J. G. Birch, M. L. Samchukov, and R. B. Ashman, "Computer–Assisted Surgery Planning for Lower Extremity Deformity Correction by the Ilizarov Method", Journal of Image Guided Surgery, 1:103–108 (1995).

M. Viceconti, A. Sudanese, A. Toni, and A. Giunti, "A Software Simulation of Tibial Fracture Reduction with External Fixator", Computer Methods and Programs in Biomedicine, 40 (1993), pp. 89–94.

Navab et al., Dynamic Geometrical Calibration for 3–D Cerebral Angiography, SPIE vol. 2708, (date unknown) pp. 361–370.

Brack et al., Towards Accurate X–Ray Camera Calibration in Computer–Assisted Robotic Surgery, 1996 Computer Assisted Radiology, pp. 721–728.

Schreiner et al., Accuracy assessment of a clinical biplane fluoroscope for three–dimensional measurements and targeting, SPIE, 1997, pp. 160–166.

Casperson, et al., Characterization of aberrations in image–intensified fluoroscopy, Medical Physics, vol. 3, No. 2, Mar./Apr. 1976, pp. 103–107.

Chakraborty, P., Image intensifier distortion correction, Medical Physics, vol. 14, No. 2, Mar./Apr. 1987, pp. 249–252.

Rudin, et al, Accurate characterization of image intensifier distortion, Medical Physics vol. 18, No. 6, Nov./Dec. 1991, pp. 1145–1151.

Champleboux, et al., Form accurate range imaging sensor calibration to accurate model–based 3–D object localization, IEEE 1992, pp. 83–89.

Champleboux, et al., Accurate Calibration of Cameras and Range Imaging Sensors: the NPBS Method, IEEE 1992, pp. 1552–1557.

Schueler, et al., Correction of image intensifier distortion for three–dimensional x–ray angiography, SPIE, vol. 2432, pp. 272–279.

Boone et al., Analysis and correction of imperfections in the image intensifier–TV—digitizer imaging chain, Medical Physics, vol. 18, No. 2, Mar./Apr. 1991, pp. 236–242.

DiGioia, et al., Mini Incision THR Assisted with Surgical Navigation, presented Fourth Annual North American Program on Computer Assisted Orthopaedic Surgery, Jun. 15–17, 2000.

Nikou, et al., Hybrid Reality Visualization Devices, presented Fourth Annual North American Program on Computer Assisted Orthopaedic Surgery, Jun. 15–17, 2000.

Nikou, et al., Augmented Reality Imaging Technology for Orthopaedic Surgery, Operative Techniques in Orthopaedics, No. 10, No. 1 (Jan. 2000), pp. 82–86.

DiGioia, III, et al., Computer Assisted Orthopaedic Surgery, Clinical Orthopaedics, vol. 354, Sep., 1998.

DiGioia III, et al., Image Guided Navigation System to Measure Intraoperatively Acetabular Implant Alignment, Clinical Orthopaedics, vol. 355, Oct., 1998.

Simon, et al., The Fundamentals of Virtual Fluoroscopy, presented Fourth Annual North American Program on Computer Assisted Orthopaedic Surgery, Jun. 15–17, 2000.

Picard, et al., Surgical Navigation: "No Pre–Operative Images Necessary", presented Fourth Annual North American Program on Computer Assisted Orthopaedic Surgery, Jun. 15–17, 2000.

Bauer, et al., Robotics for Orthopedics, presented Fourth Annual North American Program on Computer Assisted Orthopaedic Surgery, Jun. 15–17, 2000.

Abovitz, Human–Interactive Medical Robotics, presented Fourth Annual North American Program on Computer Assisted Orthopaedic Surgery, Jun. 15–17, 2000.

Bauer, et al., Pitfalls in Robotic Surgery, presented Fourth Annual North American Program on Computer Assisted Orthopaedic Surgery, Jun. 15–17, 2000.

Simon, A Framework to Evaluate Acuracy in CAOS, presented Fourth Annual North American Program on Computer Assisted Orthopaedic Surgery, Jun. 15–17, 2000.

DiGioia III, et al., Computer–Assisted tools and Interventional Technologies, The Lancet 2000, vol. 354, Dec., 1999.

Picard, et al., A Classification Proposal For Computer–Assisted Knee Systems, presented Fourth Annual North American Program on Computer Assisted Orthopaedic Surgery, Jun. 15–17, 2000.

Picard, et al., Intraoperative Navigation For TKR: Location of a Rotational Center of the Knee and Hip, presented Fourth Annual North American Program on Computer Assisted Orthopaedic Surgery, Jun. 15–17, 2000.

Miehlke, et al., Computer Integrated Instrumentation in Knee Arthroplasty, A comparative Study of Conventional and Computerized Technique, presented Fourth Annual North American Program on Computer Assisted Orthopaedic Surgery, Jun. 15–17, 2000.

Jenny, et al., Computer–Assisted Total Knee Prosthesis Implantation Without Pre–Operative Imaging, presented Fourth Annual North American Program on Computer Assisted Orthopaedic Surgery, Jun. 15–17, 2000.

Picard, et al., Kneenav—TKR: Concept and Clinical Application, presented Fourth Annual North American Program on Computer Assisted Orthopaedic Surgery, Jun. 15–17, 2000.

Kunz, et al., Advanced Intraoperative Registration of Mechanical Limb Axes for Total Knee Arthroplasty Surgery, presented Fourth Annual North American Program on Computer Assisted Orthopaedic Surgery, Jun. 15–17, 2000.

Kunz, et al., A Novel Concept for Soft Tissue Balancing and Joint Line Navigation Criteria for Tool Knee Arthroplasty, presented Fourth Annual North American Program on Computer Assisted Orthopaedic Surgery, Jun. 15–17, 2000.

Muller, et al., Computer Assisted Preoperative Planning System for Total Knee Replacement, presented Fourth Annual North American Program on Computer Assisted Orthopaedic Surgery, Jun. 15–17, 2000.

Ellis, et al., Planning and Guidance of Tibial Osteotomies: Clinical Results, presented Fourth Annual North American Program on Computer Assisted Orthopaedic Surgery, Jun. 15–17, 2000.

Sati, A Review: Robotics and Navigation Systems for Reconstructive Ligament Surgery, presented Fourth Annual North American Program on Computer Assisted Orthopaedic Surgery, Jun. 15–17, 2000.

Sati, et al., Considering Anatomic and Functional Factors in ACL Reconstruction: New Technology, presented Fourth Annual North American Program on Computer Assisted Orthopaedic Surgery, Jun. 15–17, 2000.

Stäubli, et al,, Surface Anatomy Based Realtime Navigation for ACL—Reconstruction, presented Fourth Annual North American Program on Computer Assisted Orthopaedic Surgery, Jun. 15–17, 2000.

Picard, et al., Computer–Assisted ALC Reconstruction System: Rational and Preliminary Results, presented Fourth Annual North American Program on Computer Assisted Orthopaedic Surgery, Jun. 15–17, 2000.

Luites, et al., Computer–Assisted Anatomical Placement of a Double–Bundle ACL Through 3D Fitting or a Statistically Generated Femoral Template into Individual Knee Geometry, presented Fourth Annual North American Program on Computer Assisted Orthopaedic Surgery, Jun. 15–17, 2002.

Tonet, et al., An Augmented Reality Navigation System for Computer Assisted Arthroscopic Surgery of the Knee, presented Fourth Annual North American Program on Computer Assisted Orthopaedic Surgery, Jun. 15–17, 2002.

Petermann, et al., The Caspar–System (Computer Assisted Surgery Planning and Robotics) in the ACL Reconstruction Experiences, Preliminary Results and New Developments, presented Fourth Annual North American Program on Computer Assisted Orthopaedic Surgery, Jun. 15–17, 2002.

Burkart, et al., A Method to Determine Precision and Repeatability of Tunnel Placement for ACL Reconstruction: A Comparison of Robotic and Traditional Techniques, presented Fourth Annual North American Program on Computer Assisted Orthopaedic Surgery, Jun. 15–17, 2002.

DiGioia III, Surgical Navigation and Image Guided Reconstructive Hip Surgery, presented Fourth Annual North American Program on Computer Assisted Orthopaedic Surgery, Jun. 15–17, 2002.

Lahmer, et al., Is Computer–Assisted Positioning of the Cup Necessary in Total Hip Replacement, presented Fourth Annual North American Program on Computer Assisted Orthopaedic Surgery, Jun. 15–17, 2002.

DiGioia III, et al., Unreliability of Mechanical Acetabular Alignment Guides and Ways to Improve Alignment, presented Fourth Annual North American Program on Computer Assisted Orthopaedic Surgery, Jun. 15–17, 2002.

Leenders, et al., Reduction of Abduction Angle of Acetabular Cup Position Using Computer Assisted Surgery, presented Fourth Annual North American Program on Computer Assisted Orthopaedic Surgery, Jun. 15–17, 2002.

Jaramaz, et al., Role of Bone vs. ProstheticImpingment in ROM Following THR, presented Fourth Annual North American Program on Computer Assisted Orthopaedic Surgery, Jun. 15–17, 2002.

Jaramaz, et al., HipNav Femur—Development of a Complete THR Application, presented Fourth Annual North American Program on Computer Assisted Orthopaedic Surgery, Jun. 15–17, 2002.

Jaramaz, et al., Variation in Radiographically Measured Cup Orientation, presented Fourth Annual North American Program on Computer Assisted Orthopaedic Surgery, Jun. 15–17, 2002.

Sugano, et al., Optotrak Navigation for Birmingham Hip Resurfacing, presented Fourth Annual North American Program on Computer Assisted Orthopaedic Surgery, Jun. 15–17, 2002.

Wiesel, et al., Comparison of Hand–Broached Versus Robot–Assisted Total Hip Replacement, presented Fourth Annual North American Program on Computer Assisted Orthopaedic Surgery, Jun. 15–17, 2002.

Bauer, et al., Primary and Revision THR Using the Robodoc System, presented Fourth Annual North American Program on Computer Assisted Orthopaedic Surgery, Jun. 15–17, 2002.

Decking, et al., The Caspar system for Cementless THR: Surgical Technique and Early Results, presented Fourth Annual North American Program on Computer Assisted Orthopaedics Surgery, Jun. 15–17, 2002.

Hasselbach, A Failure Protocol of the First 100 Robodoc THR, presented Fourth Annual North American Program on Computer Assisted Orthopaedic Surgery, Jun. 15–17, 2002.

Kahler, The Evolution of Computer Assisted Orthopaedic Surgery in Fracture Management, presented Fourth Annual North American Program on Computer Assisted Orthopaedic Surgery, Jun. 15–17, 2002.

Kahler, et al., Computer Guided Percutaneous Iliosacral Screw Fixation of Posterior Pelvic Ring Disruption Compared to Conventional Technique, presented Fourth Annual North American Program on Computer Assisted Orthopaedic Surgery, Jun. 15–17, 2002.

Barrick, et al., TOSCO Technique of Orthopaedic Surgery Computer Assistance Iliosacral Screw Insertion, presented Fourth Annual North American Program on Computer Assisted Orthopaedic Surgery, Jun. 15–17, 2002.

Mallik, et al., Optimizing Registration Accuracy in Computer Assisted Percutaneous Pelvic Surgery, presented Fourth Annual North American Program on Computer Assisted Orthopaedic Surgery, Jun. 15–17, 2002.

Gruetzner et al., Virtual Fluoroscopy in Acute Treatment of Pelvic Ring Disruptions, presented Fourth Annual North American Program on computer Assisted Surgery, Jun. 15–17, 2002.

Stöckle, et al., Virtual Fluoroscopy: Safe Zones for Pelvic Screw Fixations, presented Fourth Annual North American Program on Computer Assisted Orthopaedic Surgery, Jun. 15–17, 2002.

Krivonos, et al., Minimal Invasive Surgery of the Pelvis Using Ultrasound, presented Fourth Annual North American Program on Computer Assisted Orthopaedic Surgery, Jun. 15–17, 2002.

Tonetti, et al., Clinical Experience of Ultrasound Registration. Application to Percutaneous Iliosacral Screwing of the Pelvic Ring, presented Fourth Annual North American Program on Computer Assisted Orthopaedic Surgery, Jun. 15–17, 2002.

Milner, et al., Application of CT Image Guided Computer Assisted Surgical Technology in Placement of Distal Interlocking Screws, presented Fourth Annual North American Program on Computer Assisted Orthopaedic Surgery, Jun. 15–17, 2002.

Kahler, Virtual Fluoroscopy: A Tool for Decreasing Radiation Exposure During Femoral Intramedullary Nailing, presented Fourth Annual North American Program on Computer Assisted Orthopaedic Surgery, Jun. 15–17, 2002.

Sánchez, et al., A Computer Assisted Surgery System with Pre–Operative Navigation and Semi–Active Robotic Operation. Application to Traumatology and Orthopaedic Surgery, presented Fourth Annual North American Program on Computer Assisted Orthopaedic Surgery, Jun. 15–17, 2002.

Foley, et al., Virtual Fluoroscopy: Multiplanar X–Ray Guidance with Minimal Radiation Exposure, presented Fourth Annual North American Program on Computer Assisted Orthopaedic Surgery, Jun. 15–17, 2002.

Foley, et al., Virtual Fluoroscopy for Cervical Spine Surgery, presented Fourth Annual North American Program on Computer Assisted Orthopaedic Surgery, Jun. 15–17, 2002.

Merloz, et al., Computer–Assisted Surgical Navigation Using Fluoroscopy First Clinical Use in Spine Surgery, presented Fourth Annual North American Program on Computer Assisted Orthopaedic Surgery, Jun. 15–17, 2002.

Rampersaud, et al., Radiation Exposure to the Spine Surgeon During Fluoroscopically–Assisted Pedicle Screw Insertion, presented Fourth Annual North American Program on Computer Assisted Orthopaedic Surgery, Jun. 15–17, 2002.

Vandevelde, et al., Computer Planning and Image Guided Placement of Pedicle Screws for Spinal Deformities presented Fourth Annual North American Program on Computer Assisted Orthopaedic Surgery, Jun. 15–17, 2002.

Kothe, et al., Computer Navigation of Parapedicular Screw Fixation in the Thoracic Spine, presented Fourth Annual North American Program on Computer Assisted Orthopaedic Surgery, Jun. 15–17, 2002.

Tamura, et al., Registration Accuracy of Computer Aided Lumbar Spine Surgery, presented Fourth Annual North American Program on Computer Assisted Orthopaedic Surgery, Jun. 15–17, 2002.

Choi, et al., Computer Assisted Fluoroscopic Targeting System with a Robotic Arm for Pedicle Screw Insertion, presented Fourth Annual North American Program on Computer Assisted Orthopaedic Surgery, Jun. 15–17, 2002.

Pichora, et al., Case Report: A new Computer–Assisted Technique for Distal Radius Osteotomy, presented Fourth Annual North American Program on Computer Assisted Orthopaedic Surgery, Jun. 15–17, 2002.

Vandevelde, et al., The Use of Computer Assisted Technology for Navigation In Tumor Surgery, presented Fourth Annual North American Program on Computer Assisted Orthopaedic Surgery, Jun. 15–17, 2002.

Pandya, et al., The Application Accuracy of the Neuromate Robot—A Quantitative Comparison with Frameless Infrared and Frame–Based Surgical Localization Systems, presented Fourth Annual North American Program on Computer Assisted Orthopaedic Surgery, Jun. 15–17, 2002.

Hasselbach, Case Report: Computer Assisted THR in a Girdleston Hip with Malunion of the Femur, presented Fourth Annual North American Program on Computer Assisted Orthopaedic Surgery, Jun. 15–17, 2002.

Nakamura, et al., Real Time Laser–Pointing Endoscope Using Galvano Scanner and 955FPS High Speed Camera, presented Fourth Annual North American Program on Computer Assisted Orthopaedic Surgery, Jun. 15–17, 2002.

DiGioia III, Minimally Invasive Joint Resurfacing: Merging Biologics with Computer Assisted Surgical Technologies, presented Fourth Annual North American Program on Computer Assisted Orthopaedic Surgery, Jun. 15–17, 2002.

Gabriel, MicroElectroMechanical Systems (MEMS), presented Fourth Annual North American Program on Computer Assisted Orthopaedic Surgery, Jun. 15–17, 2002.

Delp, et al., Computer Assisted Knee Replacement, Clinical Orthopaedics, vol. 354, Sep., 1998, pp. 29–56.

Debski, et al., The Application of Robotics Technology to Joint Biomechanics Research, presented Fourth Annual North American Program on Computer Assisted Orthopaedic Surgery, Jun. 15–17, 2002.

Bauer, et al., Rationale for the Development of a new Robotic System for Computer Assisted Orthopedic Surgery, presented Fourth Annual North American Program on Computer Assisted Orthopaedic Surgery, Jun. 15–17, 2002.

Taylor, What does the Future Hold for the Next Generation of Medical Robotics, presented Fourth Annual North American Program on Computer Assisted Orthopaedic Surgery, Jun. 15–17, 2002.

Long, et al., 3D Model of Long Bone from Two X–Ray Images By Matching with 2D/3D Database, presented Fourth Annual North American Program on Computer Assisted Orthopaedic Surgery, Jun. 15–17, 2002.

Stäubli, et al., Gender Specific Morphometric Surface Data for Computer Assisted ACL–Navigation, presented Fourth Annual North American Program on Computer Assisted Orthopaedic Surgery, Jun. 15–17, 2002.

Fukuda, et al., High and Low Payload–Robotic Systems to Study Knee Joint Function, presented Fourth Annual North American Program on Computer Assisted Orthopaedic Surgery, Jun. 15–17, 2002.

Gerhardt, et al., Improved Quality Control in Total Hip Replacement by the Finite Element Method Based on Computer Assisted Preoperative Planning, presented Fourth Annual North American Program on Computer Assisted Orthopaedic Surgery, Jun. 15–17, 2002.

Messmer, et al., Interactive Preoperative Planning of Internal Fixation on a Virtual 3D Model, presented Fourth Annual North American Program on Computer Assisted Orthopaedic Surgery, Jun. 15–17, 2002.

Malvisi, et al., Milling Bone: Comparison of the Temperature Elevation and Clinical Performances During Cutting, presented Fourth Annual North American Program on Computer Assisted Orthopaedic Surgery, Jun. 15–17, 2002.

Firoozbakhsh, et al., Pelvis Image Guided Surgery Phantom Study, presented Fourth Annual North American Program on Computer Assisted Orthopaedic Surgery, Jun. 15–17, 2002.

Robertson, et al., The Sensitivity of Carpal Bone Indices to Rotation Determined Using Digitally Reconstructed Radiographs, presented Fourth Annual North American Program on Computer Assisted Orthopaedic Surgery, Jun. 15–17, 2002.

Murphy, Total Hip Anthroplasty with an Uncemented Femoral Component Using Intra–Operative Machining, presented Fourth Annual North American Program on Computer Assisted Orthopaedic Surgery, Jun. 15–17, 2002.

COMPUTER-AIDED BONE DISTRACTION

CROSS REFERENCE TO RELATED APPLICATIONS (Not Applicable)

STATEMENT REGARDING FEDERALLY SPONSORED RESEARCH OR DEVELOPMENT (Not Applicable)

BACKGROUND OF THE INVENTION

1. Field of the Invention

The present invention broadly relates to the field of orthopedic surgery, and more particularly, to computer assisted orthopedic surgery that uses two or more X-ray images of a patient's bone to generate a computer-based 3D (three dimensional) model of the patient's bone and a computer-based surgical plan for the doctor.

2. Description of the Related Art

Bone distraction in orthopedic surgery might well be considered one of the earliest successful forms of tissue engineering. Bone distraction is a therapeutic process invented in Russia in about 1951 for treating fractures, lengthening limbs and correcting other skeletal defects such as angular deformities. In bone distraction, external fixators are used to correct bone deformities and to lengthen bones by the controlled application of 'tension-stress', resulting in natural, healthy tissue.

FIG. 1 illustrates a prior art Ilizarov fixator 20 attached to a bone 22. The external Ilizarov fixator 20 is constituted of a pair of rings 24 separated by adjustable struts 28. The rings 24 are mounted onto the bone 22 from outside of the patient's body through wires or half-pins 26 as illustrated in FIG. 1. The lengths of the struts 28 can be adjusted to control the relative positions and orientations of the rings 24. After the fixator 20 is mounted to the patient's bone 22, the bone 22 is cut by osteotome (i.e., surgical cutting of a,bone) as part of the bone distraction process. Thereafter, the length of each individual strut 28 is adjusted according to a surgical plan. This length adjustment results in the changing of the relative position of the rings 24, which then forces the distracted (or "cut") bone ends to comply and produce new bone in-between. This is termed the principle of "tension-stress" as applied to bone distraction.

The bone distraction rate is usually controlled at approximately 1 mm (millimeter) per day. The new bone grows with the applied distraction and consolidates after the distraction is terminated. Thereafter, the fixator 20 can be safely removed from the bone 22 and, after recanalization, the new or "distracted" bone is almost indistinguishable from the old or pre-surgery bone. The bone 22 may be equipped with other units, such as hinges, to correct rotational deformities about one or a few fixed axes. Thus, controlled application of mechanical stress forces the regeneration of the bone and soft tissues to correct their own deformities. The whole process of deformity correction is known as "bone distraction."

At present, the following nominal steps are performed during the bone distraction process: (1) Determine an appropriate frame size for the fixator (e.g., for the Ilizarov fixator 20); (2) Measure (e.g., from X-rays) the deformity of bone fragments (or the anticipated fragments after surgically cutting the bone) and obtain six parameters that localize one fragment relative to the other; (3) Determine (or anticipate) how the fixator frame should be mounted on the limb; (4) Input the parameters and measurements to a computer program that generates the strut lengths as a function of time required to correct the deformity; (5) Mount the fixator frame onto the bone fragments; and (6) Adjust the strut lengths on a daily basis according to the schedule generated in step (4).

The steps outlined in the preceding paragraph are currently executed with minimal computerized assistance. Typically, surgeons manually gather or determine the required data (e.g., fixator frame size, bone dimensions, fixator frame mounting location and orientation, etc.) and make their decisions based on hand-drawn two-dimensional sketches or using digitized drawings obtained by tracing X-ray images For example, a computerized deformity analysis (CDA) and pre-operative planning system (hereafter "the CDA system") developed by Orthographics of Salt Lake City, Utah, USA, rates the boundary geometry of bones using X-ray images that are first digitized manually, i.e., by placing an X-ray image on a light table and then tracing the outline with a digitizing stylus, and then the digital data are fed into the CDA system. Thereafter, the CDA system assists the surgeon in measuring the degree of deformity and to make a surgical plan. The entire process, however, is based on two-dimensional drawings and there is no teaching of showing or utilizing three-dimensional bone deformity or bone geometry.

It is observed that in the complex area of bone distraction surgery, it is difficult, if not impossible, to make accurate surgical plans based solely on a limited number of two-dimensional renderings of bone geometry. This is because of the complex and inherently three-dimensional nature of bone deformities as well as of fixator geometry. Furthermore, two-dimensional depictions of surgical plans may not accurately portray the complexities involved in accessing the target positions of the osteotome and fixator pins surrounding the operated bone. Lack of three-dimensional modeling of these geometric complexities makes it difficult to accurately mount the fixator on the patient according to the pre-surgical plan.

After a surgeon collects the requisite data (e.g., fixator frame size to be used, patient's bone dimensions, fixator frame mounting location and orientation, etc.), the surgeon may use the simulation software accompanying commercially available fixators (such as the Taylor Spatial Frame distributed by Smith & Nephew Inc. of 1450 Brooks Road, Memphis, Tenn., USA 38116) to generate a day-by-day plan that shows how the lengths of the fixator struts should be adjusted. Such a plan is generated after the initial and target frame positions and orientations are specified by the surgeon. However, the only functionality of the simulation software is a simple calculation of the interpolated frame configurations. The software does not provide any assistance to the surgeon about making surgical plans nor does it provide any visual feedback on how the fixator frame and bone fragments should be moved over time.

The Taylor Spatial Frame (shown, for example, in FIG. 16) with six degrees of freedom (DOF) is more versatile, flexible and complex than the Ilizarov fixator 20 in FIG. 1. Because of the sophistication of modern fixators (e.g., the Taylor Spatial Frame) and because of the limitations of the presently available bone distraction planning and execution systems, current computerized bone distraction procedures are error-prone, even when performed by the most experienced surgeons. As a result, the patients must typically revisit the surgeon several times after the initial operation in order for the surgeon to re-plan and refine the tension-stress schedule, or even to re-position the fixator. Such reiterations of surgical procedures are not only time-consuming, but incur additional costs and may lead to poorer therapeutic results while unnecessarily subjecting patients to added distress. It is therefore desirable to generate requisite bone and fixator models in three-dimensions prior to surgery so as to minimize the surgery planning and execution errors mentioned hereinbefore.

The discussion given hereinbelow describes some additional software packages that are available today to assist in the simulation and planning of bone distraction. However, it is noted at the outset that these software packages are not based on three-dimensional models. Further, these software packages are quite limited in their capabilities to assist the surgeon in making important clinical and procedural decisions, such as how to access the site of the osteotomy or how to optimally configure fixator pin configurations. Additional limitations of the present software systems include: (1) No realistic three-dimensional view of a bone and a fixator; (2) No usage of motion in surgical simulation; (3) Lack of an easy-to-use graphical user interface for user-friendliness; (4) No on-line database of standard or past similar cases and treatment data; and (5) No file input/output to store or retrieve previous case data.

In "Correction of General Deformity With The Taylor Spatial Frame Fixator™" (1997), Charles J. Taylor refers to a software package from Smith & Nephew (Memphis, Tenn.) (hereafter "the Smith software") that utilizes the Taylor Spatial Frame for certain computations. However, the Smith software does not include any visual output to the user (i.e., the surgeon) and user needs to enter all data via a dialog box. Being mechanical in nature, the strut locations in a fixator are static. However, the Smith software does not account for whether a strut can be set to all the lengths necessary during the bone correction process. Further, the Smith software cannot calculate corrections that are due to malrotation (of the fixator) only.

As described hereinbefore, a software for computerized bone deformity analysis and pre-operative planning is developed by Orthographics of Salt Lake City, Utah, USA (hereafter "the Orthographics software"). The Orthographics software creates the boundary geometry of bones using X-ray images that are first digitized manually as previously mentioned. Thereafter, the Orthographics software assists the surgeon in measuring the degree of bone deformity and to make a surgical plan. The entire process, however, is based on two-dimensional drawings and there is no support for showing or utilizing three-dimensional bone deformity or bone geometry. However, it is difficult to make accurate surgical plans based on a few such two-dimensional renderings considering the complex, three-dimensional nature of bone deformities and fixator geometry, and also considering he complexity involved in accessing the target positions of the osteotomy and fixator pins. This inherently three-dimensional nature of bone geometry and fixator assembly also makes it difficult to accurately mount the fixator on the patient's bone according to the two-dimensional pre-surgical plan. For further reference, see D. Paley, H. F. Kovelman and J. E. Herzenberg, Ilizarov Technology, "Advances in Operative Orthopaedics," Volume 1, Mosby Year Book. Inc., 1993.

The software developed by Texas Scottish Rite Hospital for Children utilizes primitive digitization of the radiographs to generate three-dimensional representations of bones without any simulation. Additionally, the generated models are very primitive and do not show any kind of detail on the bone. For further reference, see Hong Lin, John G. Birch, Mikhail L. Samchukov and Richard B. Ashman, "Computer Assisted Surgery Planning For Lower Extremity Deformity Correction By The Ilizarov Method," Texas Scottish Rite Hospital for Children.

The SERF (Simulation Environment of a Robotic Fixator) software has capability to represent a three-dimensional bone model. However, the graphical representations of the fixator frame and the bone by the SERF software are over-simplified. Furthermore, there is no mention of any user interface except for a dialog box that prompts a user (e.g., a surgeon) for a "maximum distance." Additional information may be obtained from M. Viceconti, A. Sudanese, A. Toni and A. Giunti, "A software simulation of tibial fracture reduction with external fixator," Laboratory for Biomaterials Technology, Istituto Rizzoli, Bologna, Italy, and Orthopaedic Clinic, University of Bologna, Italy, 1993.

In "Computer-assisted preoperative planning (CAPP) in ortiopaedic surgery," Orthopaedic Hospital, Medical College, University of Zagreb, Yugoslavia, 1990, Vilijam Zdravkovic and Ranko Bilic describe a CAPP and Computer Assisted Orthopedic Surgery system. The system receives feedback and derives a bone's geometry from two two-dimensional scans. However, this system still uses the less sophisticated and less complex Ilizarov fixator 20 (FIG. 1) instead of the more advanced Taylor Spatial Frame.

In a computer-assisted surgery, the general goal is to allow the surgeon to accurately execute the pre-operative plan or schedule. One approach to fulfil this goal is to provide feedback to the surgeon on the relative positions and the orientations of bone fragments, fixator frame and osteotomy/coricotomy site as the surgical procedure progresses. These positions could be determined in real time by measuring, with the help of an infrared (R) tracking system, the positions of infrared light emitting diode (LED) markers strategically placed on the fixator frame, on cutting tools and on the patient. The relative positions of all these objects (and deviations from the planed positions) could then be displayed via a computerized image simulation to give guidance to the surgeon operating on the patient. Such a feedback approach is currently used to help register acetabular implants in artificial hip surgery using an Optotrak optical tracking camera from Northern Digital Inc. of Ontario, Canada. The Optotrak camera is capable of tracking the positions of special LEDs or targets attached to bones, surgical tools and other pieces of operating room equipment. However, for use in a computer-aided bone distraction system, the Optotrak camera and additional display hardware are too expensive to consider for a widespread bone distraction commercialization strategy.

It is estimated that, at present, less than 1% of orthopedic surgeons practice the bone distraction procedure and less than 5000 bone distraction cases are performed per year worldwide. Such relative lack of popularity may be attributed to the fact that learning the techniques for bone distraction is extremely demanding and time-consuming. Therefore, the average orthopedic surgeon does not perform these techniques. Thus, there is a significant number of patients for whom external fixation with distraction would be the treatment of choice, but because of the current complexity and cost limitations, these patients never benefit from advanced bone distraction procedures.

It is therefore desirable to develop a user-friendly (i.e., a surgeon-friendly) system that would make bone distraction a viable option for a much broader market of surgeons than are currently using this therapy. It is also desirable to devise a computer-based surgical planning service that simplifies frame fixation, decreases preoperative planning time and reduces the chances of complications, thereby making far fixation a relatively physician-friendly technique. To facilitate acceptance of complex bone distraction procedures to a wider segment of orthopedic surgeons, it is further desirable to overcome two primary limitations present in current surgical planning and execution software: (1) the lack of three-dimensional visual aids and user-friendly simulation tools, and (2) the lack of an accurate and economical registration (i.e., fixator mounting) scheme.

SUMMARY OF THE INVENTION

The present invention contemplates a method of generating a computer-based 3D (three dimensional) model for a patient's anatomical part comprising defining a 3D template model for the patient's anatomical part; receiving a plurality of 2D (two dimensional) x-ray images of the patient's anatomical part; extracting 2D fiducial geometry of the patient's anatomical part from each of said plurality of 2D x-ray images; and deforming the 3D template model using the 2D fiducial geometry of the patient's anatomical part so as to minimize an error between contours of the patient's anatomical part and those of the deformed 3D template model.

A computer assisted orthopedic surgery planner software according to the present invention may identify the 2D fiducial geometry of a patient's bone (or other anatomical part under consideration) on the 3D template bone model prior to deforming the 3D template bone model to substantially conform to the contours of the actual patient's bone. In one embodiment, after detecting the bone contour, the computer assisted orthopedic surgery planner software creates a 3D lattice in which the 3D template bone model is embedded. Thereafter, a free-form deformation process is applied to the 3D lattice to match with the contour of the patient's bone, deforming the 3D template bone model in the process. Sequential quadratic programing (SQP) techniques may be used to minimize error between 2D X-ray images data and the deformed template bone data.

In an alternative embodiment, a template polygonal mesh representing a standard parametric geometry and topology of a bone is defined. The template polygonal mesh is then converted into a deformable model consisting of a system of stretched springs and bent springs. Then, multiple X-ray images of the patient's bone are used to generate force constraints that deform and resize the deformable model until the projections of the deformed bone model conform to the input X-ray images. To further assist the bone geometry reconstruction problem, a standard library of image processing routines may be used to filter, threshold and perform edge detection to extract two-dimensional bone boundaries from the X-ray images.

In another embodiment, the present invention contemplates a computer-based method of generating a surgical plan comprising reading digital data associated with a 3D (three-dimensional) model of a patient's bone, wherein the digital data resides in a memory in a computer; and generating a surgical plan for the patient's bone based on an analysis of the digital data associated with the 3D model. A surgical planner/simulator module in the computer assisted orthopedic surgery planner software makes a detailed surgical plan using realistic 3D computer graphics and animation. The simulated surgical plan may be viewed on a display seen of a personal computer. The planner module may also generate a pre-surgery report documenting various aspects of the bone surgery including animation of the bone distraction process, type and size of fixator frame and its struts, a plan for mounting the fixator frame on the patient's bone, the location of the osteotomy/coricotomy site and the day-by-day length adjustment schedule for each fixator strut.

In a still further embodiment, the present invention contemplates an arrangement wherein a computer assisted orthopedic surgery planner computer terminal is connected to a remote operation site via a communication network, e.g., the Internet. The computer assisted orthopedic surgery planner software may be executed on the computer assisted orthopedic surgery planner computer. A fee-based bone distraction planning (BDP) service may be offered via a network (e.g., the Internet) using the computer assisted orthopedic surgery planner software at the service provider's site. An expert surgeon at the service provider's site may receive a patient's X-ray data and other additional information from a remotely-located surgeon who will be actually operating on the patient. The remotely-located surgeon may be a subscriber to the network-based BDP service. The expert surgeon may analyze the X-ray data and other patient-specific medical data supplied by the remotely-located surgeon with the help of the computer assisted orthopedic surgery planner software executed on the computer assisted orthopedic surgery planner computer. Thereafter, the expert surgeon may send to the remotely-located surgeon over the Internet the 3D bone model of the patient's bone, a simulated surgery plan as well as a complete bone distraction schedule generated with the help of the computer assisted orthopedic surgery planer software of the present invention.

The computer assisted orthopedic surgery planner software of the present invention makes accurate surgical plans based solely on a number of two-dimensional renderings of the patient's bone geometry. The software takes into account the complex and inherently three-dimensional nature of bone deformities as well as of fixator geometry. Furthermore, three-dimensional simulation of the suggested surgical plan realistically portrays the complexities involved in accessing the target positions of the osteotome and fixator pins surrounding the operated bone, allowing the surgeon to accurately mount the fixator on the patient according to the pre-surgical plan.

With the computer-aided pre-operative planning and frame application and adjustment methods of the present invention, the duration of fixation (of a fixator frame) may be reduced by an average of four to six weeks. Additionally, by lowering the frequency of prolonged fixations, substantial cost savings per patient may be achieved. Shortening of the treatment time and reduction of complications may lead to better surgical results and higher patient satisfaction. The use of the computer assisted orthopedic surgery planner software of the present invention (e.g., in an Internet-based bone distraction surgery planning service) may make the frame fixation and bone distraction processes physician-friendly by simplifying fixation, decreasing preoperative planning time, and reducing the chances of complications through realistic 3D simulations and bone models. Thus more surgeons may practice bone distraction, resulting in benefits to more patients in need of bone distraction.

BRIEF DESCRIPTION OF DRAWINGS

Further advantages of the present invention may be better understood by referring to the following description taken in conjunction with the accompanying drawings, in which.

DETAILED DESCRIPTION OF PREFERRED EMBODIMENTS

Figure 2:
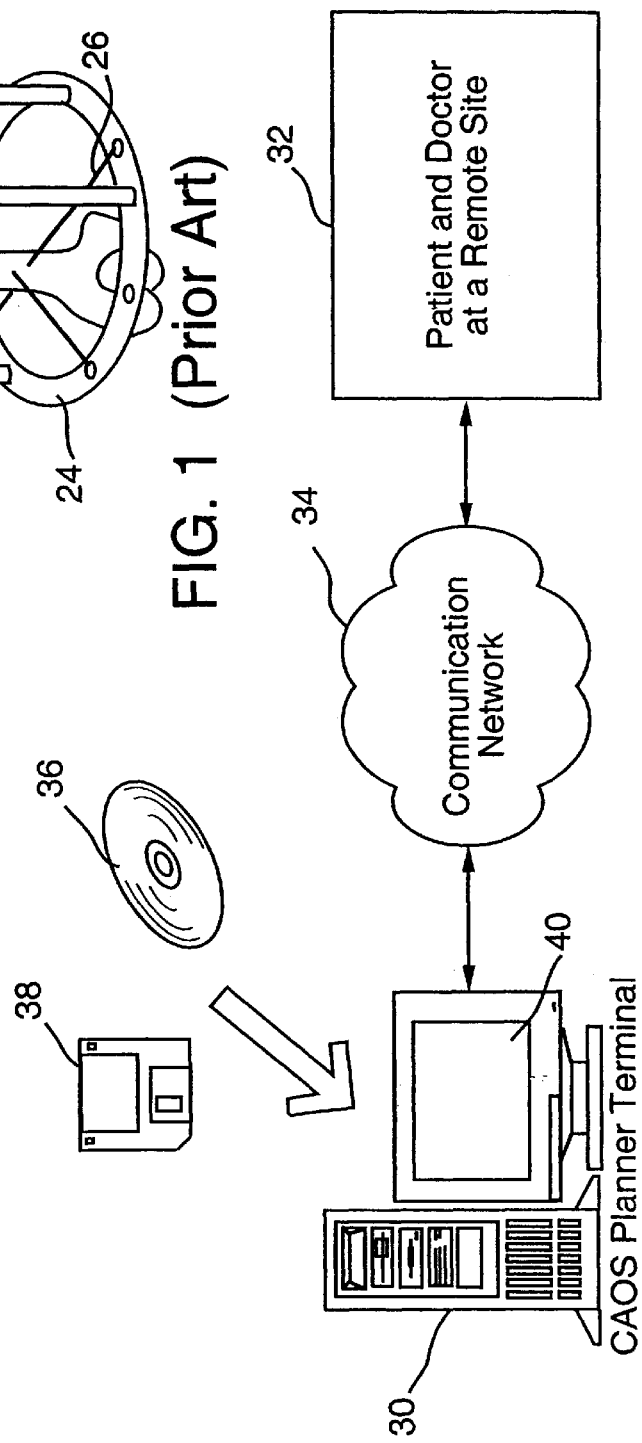
FIG. 2 depicts an exemplary setup to perform computer assisted orthopedic surgery according to the present invention.

FIG. 2 depicts an exemplary setup to perform computer assisted orthopedic surgery according to the present invention. A computer assisted orthopedic surgery planner computer 30 is accessible to a surgeon in a remote operation site 32 via a communication network 34. In one embodiment, the communication network 34 may be an ethernet LAN (local area network) connecting all the computers within an operating facility, e.g., a hospital. In that case, the surgeon and the computer assisted orthopedic surgery terminal 30 may be physically located in the same site, e.g., the operating site 32. In alternative embodiments, the communication network 34 may include, independently or in combination, any of the present or future wireline or wireless data communication network, e.g., the Internet, the PSTN (public switched telephone network), a cellular telephone network, a WAN (wide area network), a satellite-based communication link, a MAN (metropolitan area network) etc.

The computer assisted orthopedic surgery planner computer 30 may be, e.g., a personal computer (PC) or nay be a graphics workstation. Similarly, the doctor at the remote site 32 may have access to a computer terminal (not shown) to view and manipulate three-dimensional (3D) bone and fixator models transmitted by the computer assisted orthopedic surgery planner computer 30. In one embodiment, the computer assisted orthopedic surgery planner terminal 30 may function as the surgeon's computer when the operating site includes the computer assisted orthopedic surgery planner computer 30. Each computer—the computer assisted orthopedic surgery planner computer 30 and the remote computer (not shown) at the operating site—may include requisite data storage capability in the form of one or more volatile and non-volatile memory modules. The memory modules may include RAM (random access memory), ROM (read only memory) and HDD (hard disk drive) storage. Memory storage is desirable in view of sophisticated computer simulation and graphics performed by the computer assisted orthopedic surgery planner software according to the present invention.

The computer assisted orthopedic surgery planner software may be initially stored on a portable data storage medium, e.g., a floppy diskette 38, a compact disc 36, a data cartridge (not shown) or any other magnetic or optical data storage. The computer assisted orthopedic surgery planner computer 30 may include appropriate disk drives to receive the portable data storage medium and to read the program code stored thereon, thereby facilitating execution of the computer assisted orthopedic surgery planner software. The computer assisted orthopedic surgery planner software, upon execution by the computer assisted orthopedic surgery planner computer 30, may cause the computer assisted orthopedic surgery computer 30 to perform a variety of data processing and display tasks including, for example, display of a 3D bone model of the patient's bone on the computer screen 40, rotation (on the screen 40) of the 3D bone model in response to the commands received from the user (i.e., the surgeon), transmitting the generated 3D bone model to the computer at the remote site 32, etc.

Before discussing how the computer assisted orthopedic surgery planner software generates 3D bone and fixator models and simulates surgical plans for bone distraction, it is noted that the arrangement depicted in FIG. 2 may be used to provide a commercial, network-based bone distraction planning (BDP) service. The network may be any communication network 34, e.g., the Internet. In one embodiment, the surgeon performing the bone distraction at the remote site 32 may log into the BDP service provider's website and then send X-ray images, photographs and/or video of the patient's bone along with pertinent patient history to an expert surgeon located at and operating the computer assisted orthopedic surgery computer 30. The expert surgeon may then assess the case to determine if distraction is a viable option and, if so, then use the computer assisted orthopedic surgery planner software residing on the computer assisted orthopedic surgery computer terminal 30 to help plan the distraction process. The expert surgeon may transmit the distraction plan, simulation videos and distraction schedule—all generated with the help of the computer assisted orthopedic surgery planner software according to the present invention—to the service user (i.e., the surgeon at the remote site 32). Such a network-based bone distraction planning and consultancy service may be offered to individual surgeons or hospitals on a fixed-fee basis, on a per-operation basis or on any other payment plan mutually convenient to the service provider and the service recipient.

In an alternative embodiment, the network-based bone distraction planning service may be implemented without the aid of the computer assisted orthopedic surgery planner software of the present invention. Instead, the expert surgeon at the computer assisted orthopedic surgery planner terminal 30 may utilize any other software or manual assistance (e.g., from a colleague) to efficiently evaluate the bone distraction cm at hand and to transit the response back to the surgeon or user at the remote site 32.

Figure 3:
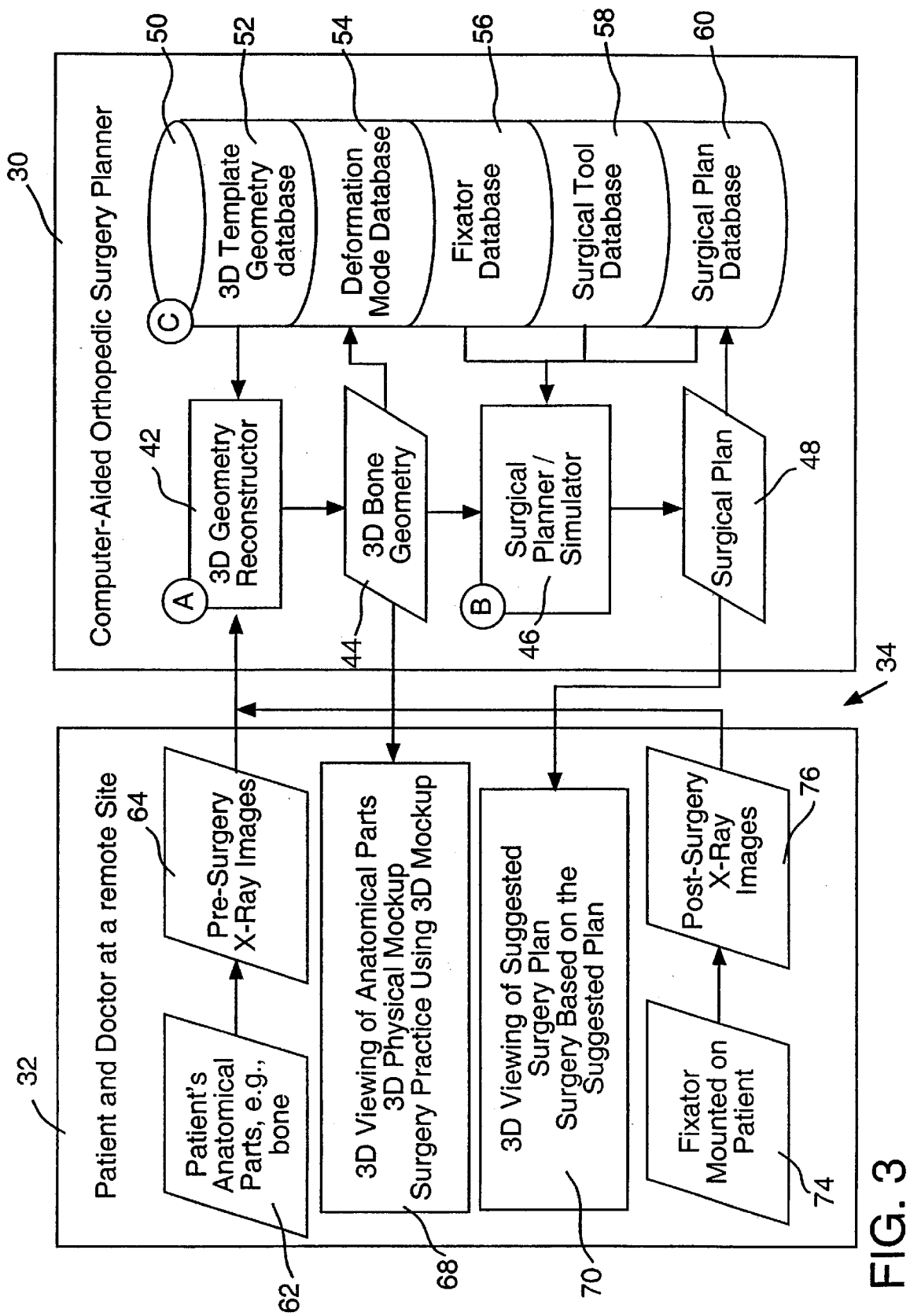
FIG. 3 shows an exemplary operational block diagram for the three modules constituting the computer assisted orthopedic surgery planner software according to the present invention.

FIG. 3 shows an exemplary operational block diagram for the three modules constituting the computer assisted orthopedic surgery planner software according to the present invention. The three modules are denoted by circled letters A, B and C. Module A is a 3D geometry reconstuctor module 42 that can generate a 3D bone geometry (as shown by the data block 44) from 2D (two-dimensional) X-ray images of the patient's bone as discussed hereinbelow. Module B is a surgical planner/simulator module 46 that can prepare a surgical plan for bone distraction (as shown by the data block 48). Finally, module C is a database module 50 that contains a variety of databases including, for example, a 3D template geometry database 52, a deformation mode database 54, a fixator database 56, a surgical tool database 58 and a surgical plan database 60. All of these modules arm shown residing (in a suitable memory or storage area) in the computer assisted orthopedic surgery planner terminal 30. The discussion hereinbelow focuses on modules A, B and C; however, it is understood that these modules do not function independently of a platform (here, the computer assisted orthopedic surgery planner computer 30) that executes the program code or instructions for the respective module. In other words, the screen displays and printouts discussed hereinbelow may be generated only after the program code for a corresponding module is executed by the computer assisted orthopedic surgery planner computer 30.

The 3D geometry reconstructor module (or module A) 42 according to the present invention reconstructs three-dimensional bone geometry using free-form deformation (FFD) and sequential quadratic programming (SQP) techniques. Module A also generates relative positions and orientations of the patient's bone and the fixator mounted thereon. The surgical planner/simulator module (or module B) 46 provides a user-friendly simulation and planning environment using 3D, interactive computer graphics. Module B can show a realistic image of the bones, fixator and osteotomy/coricotomy, while the bone lengthening and deformity correction process is animated with 3D graphics. The database module (or module C) 50 aids in the measurement of the relative positions of the mounted fixator, osteotomy/coricotomy, and bones and feeds this information back into the computer assisted orthopedic surgery planner software to determine the final daily distraction schedule.

As an overview, it is noted that the 3D geometry reconstructor module 42 takes two (or more than two) X-ray images of patient's bone, wherein the X-ray images are taken from two orthogonal directions. Module A 42 starts with a predefined three-dimensional template bone shape, whose shape is clinically normal and is scaled to an average size. Module A 42 then scales and deforms the template shape until the deformed shape gives an image similar to an input X-ray image when projected onto a two-dimensional plane. Hierarchical free-form deformation (FFD) may be used to scale and deform the template bone, wherein the deformation in each deformation layer may be controlled by a number of variables (e.g., eight variables). Thus, the problem of finding the three-dimensional shape of the bone is reduced to an optimization problem with eight design variables. Therefore, one objective of module A 42 is to minimize the error, or the difference, between the input X-ray image and the projected image of the deformed template shape. SQP (sequential quadratic programming) techniques may be used to solve this multi-dimensional optimization problem. In other words, SQP techniques may be applied to calculate optimized FFD parameters for least error.

Generation of a 3D model of a patient's bone (or any other anatomical part) based on two or more X-ray images of the bone allows for efficient pre-, intra-, and post-operative surgical planning. It is noted that X-ray image-based shape reconstruction (e.g., generation of 3D models of an anatomical part) is more computationally efficient, cost effective and portable as compared to image processing using standard three-dimensional sensor-based methods, such as MRI (magnetic resonance imaging) or CAT (computerized axial tomography). The three-dimensional shapes generated by Module A 42 may be useful in many applications including, for example, making a three-dimensional physical mockup for surgery training or importing into and using in a computer-aided planning system for orthopedic surgery including bone distraction and open/closed wedge osteotomy. Furthermore, module A may reconstruct the 3D geometric model of the bone even if there are partially hidden bone boundaries on X-ray images.

Using CAT or MRI data for reconstructing bone geometry, however, has several practical limitations. First, compared to X-ray images, CAT and MRI are not cost or time effective, which may inhibit widespread clinical usage. X-ray imaging is available not only in large medical institutes, but also in smaller medical facilities that cannot afford CAT or MRI equipment. Second, X-ray imaging is portable so that it can be used in a remote site, even in a battlefield. In addition, the cost of scanning each patient using CAT or MRI is high, and the procedure is time consuming. Another disadvantage of using MRI or CAT is associated with the robustness of the software that performs surface geometry extraction. CAT or MRI's volumetric data has a much lower resolution compared to X-ray images, and the surface extraction process often cannot be completed due to the low resolution. Finally, X-ray imaging is preferred for imaging osseous tissues.

Because there is an unknown spatial relationship between the pre-operative data (e.g., medical or X-ray images, surgical plans, etc.) and the physical patient on the operating room table, the 3D geometry reconstructor module 42 provides for both pre-operative and intra-operative registration of orthopedic bone deformity correction. A 3D solid model of the bone generated by module A 42 (as shown by data block 44 in FIG. 3 and 3D bone image 67 in FIG. 4) may function as a fundamental tool for pre-, intra-, and post-operative surgical planning. The 3D geometry reconstructor module 42 develops interactive, patient-specific pre-operative 3D bone geometry to optimize performance of surgery and the subsequent biologic response.

Figure 4:
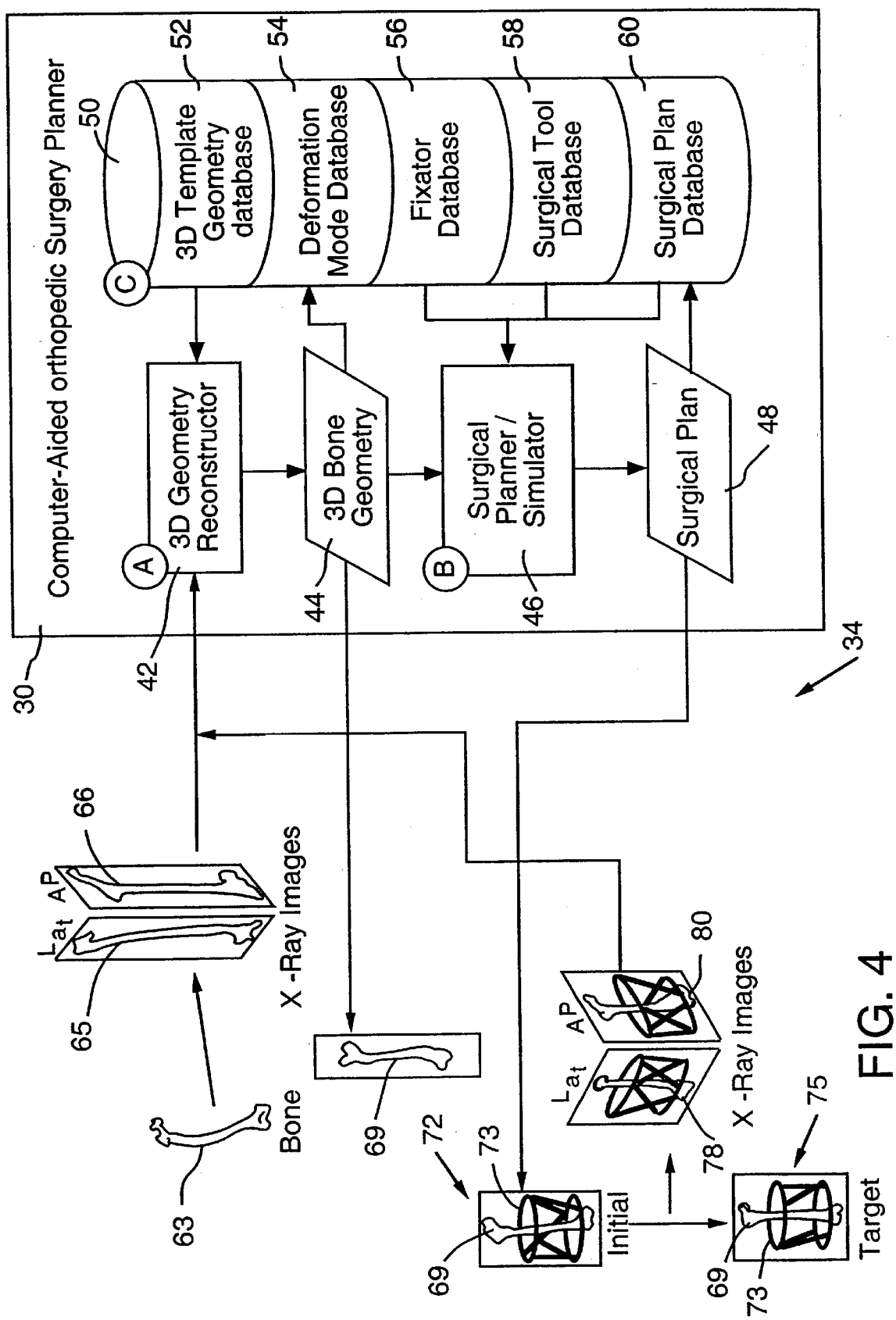
FIG. 4 graphically illustrates exemplary computer screen displays generated upon execution of the computer assisted orthopedic surgery planner software of the present invention.
Figure 5:
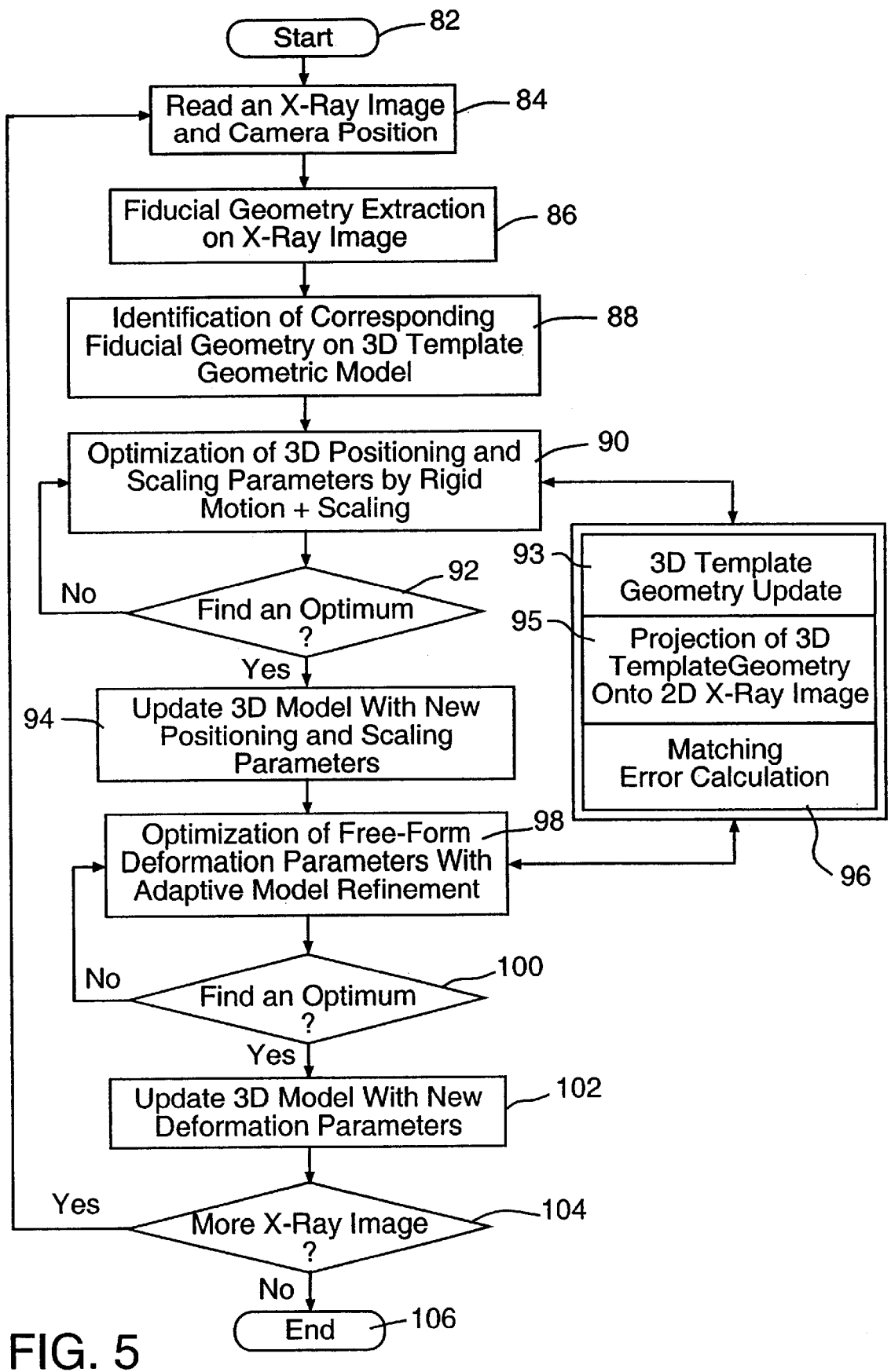
FIG. 5 is an exemplary flowchart depicting operational steps performed by the 3D geometry reconstructor module of the computer assisted orthopedic surgery planner software.

FIG. 4 graphically illustrates exemplary computer screen displays generated upon execution of the computer assisted orthopedic surgery planner software of the present invention. FIGS. 3 and 4 may be viewed together to better understand the functions performed by modules A, B and C, and also to have a visual reference of various 3D models generated by the computer assisted orthopedic surgery planner software according to the present invention. Furthermore, FIG. 5 is an exemplary flowchart depicting operational steps performed by the 3D geometry reconstructor module 42 of the computer assisted orthopedic surgery planner software. The following discussion will also refer to various operational steps in FIG. 5 as appropriate.

Initially, at block 62, a surgeon determines (at a remote site 32) which of the patient's anatomical parts (e.g., a bone) is to be operated on. FIG. 4 shows a bone 63 that is to be distracted. Thereafter, at block 64, the surgeon or an assistant of the surgeon prepares digitized X-ray images for various X-ray views of the patient's bone 63. Digitization may be carried out manually, e.g., by placing an X-ray image on a light table and then tracing the outline of the bone contour with a digitizing stylus. In the embodiment illustrated in FIG. 4, digitized versions of a lateral (Lat) X-ray image 65 and an anterior/posterior (AP) X-ray image 66 of the bone 63 are input to the computer assisted orthopedic surgery planner software via the communication network 34 interconnecting the remote patient site 32 and the computer assisted orthopedic surgery planner terminal 30. It is noted that the X-ray images 65,66 represent bone geometry in two-dimensional (2D) views.

Upon execution of module A (at step 82 in FIG. 5), module A 42 receives (at block 84 in FIG. 5) as input the digitized X-ray images 65,66. It is assumed that the X-ray images 65,66 are taken from two orthogonal directions, usually front (or AP) and side (or lateral). This constraint of the orthogonal camera positions is a strong one, but it may be loosened, if necessary, with the modification of deformation parameters and extra computational cost in the optimization process. Module A 42 may also receive positional data for the X-ray camera (not shown) with reference to a pre-determined coordinate system. Such coordinate position may be useful for module A 42 to "read" the received X-ray 65,66 in proper geometrical context. A user, e.g., the operator of the X-ray camera, may manually input the camera position coordinates and viewing angle data. Alternatively, a scheme may be devised to automatically incorporate the camera position parameters and viewing angle data as a set of variables to be optimized during the optimization process discussed hereinbelow. More than two X-ray images could be added to the input if greater accuracy is required or if a certain part of the bone that is hidden in the AP and lateral views plays an important role in the bone distraction procedure. Since MRI and CAT have volumetric data set, using X-ray images to reconstruct the bone structure (e.g., the 3D geometric module 69) is more cost-effective and less time-consuming.

After receiving the 2D X-ray images 65,66, the 3D geometry reconstructor module 42 may extract at step 86 the fiducial geometry (or bone contour) from the X-ray images. The 2D X-ray images 65,66 represent the bone contour with a set of characteristic vertices and edges with respect to the respective X-ray image's coordinate system. In one embodiment, an operator at the computer assisted orthopedic surgery planner terminal 30 may manually choose (with the help of a keyboard and a pointing device, e.g., a computer mouse) the bone contour from the 2D X-ray images 65,66 of the bone 63 displayed on the computer screen 40. In another embodiment, commercially available edge detection software may be used to semi-automate the fiducial geometry extraction process.

Figure 6:
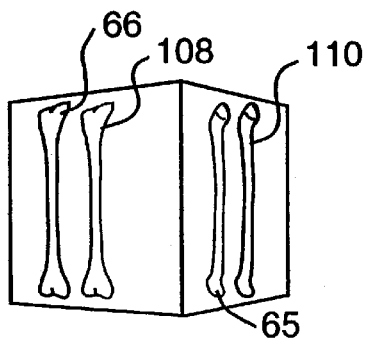
FIG. 6 shows front and side X-ray images of a bone and corresponding bone boundaries extracted therefrom.
Figure 7:
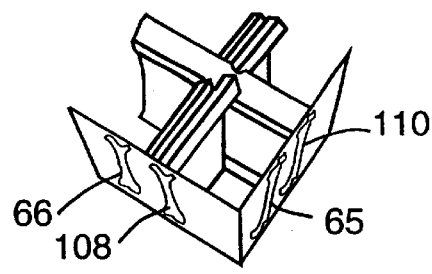
FIG. 7 portrays intersection of swept bone boundaries shown in FIG. 6.

After, before or simultaneous with the fiducial geometry extraction, module A 42 may access the 3D template geometry database 52 to select a 3D template bone model (not shown) that may later be deformed with the help of the 2D X-ray images 65,66 of the patient's bone 63. The size (or outer limits) of the 3D template bone model may be selected based on the computation of the closed volume that tightly bounds the patient's bone geometry. FIGS. 6 and 7 illustrate certain of the steps involved in that computation. FIG. 6 shows front (66) and side (65) X-ray images of a bone and corresponding bone boundaries (108 and 110 respectively) extracted therefrom. FIG. 7 portrays the intersection of swept bone boundaries 108, 110 shown in FIG. 6. The intersection of the bone boundaries defines a closed volume that may tightly bound the 3D template bone model and that closely resembles the volumetric dimensions of the patient's bone.

Figure 8:
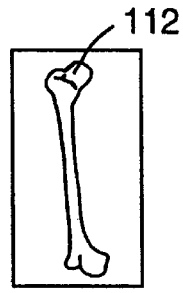
FIG. 8 displays an undeformed 3D template bone model with the patient's bone geometry reconstructed thereon.

After detecting the bone contour at step 86, module A 42 first identifies (at step 88) the corresponding fiducial geometry on the 3D template bone model prior to any deformation discussed hereinbelow. Module A 42 also optimizes (at steps 90 and 92) the 3D positioning and scaling parameters for the 3D template bone model until the size and position of the 3D template bone model is optimum with respect to the patient's bone 63 (as judged from the X-ray images 65,66 of the patient's bone 63). Upon finding the optimum values for positioning and scaling parameters, module A 42 updates (at step 94) the 3D template bone model with new positioning and scaling parameters. The resultant 3D template bone model 112 is shown in FIG. 8, which displays the undeformed 3D template bone model 112 with the patient's bone geometry reconstructed thereon. Module A 42 may also update (block 93) the 3D template geometry database 52 with the optimum positioning and scaling parameter values computed at steps 90 and 92 for the selected template bone model. Thus, the 3D template geometry database 52 may contain 3D template bone models that closely resemble actual, real-life patients' bones.

Figure 9A:
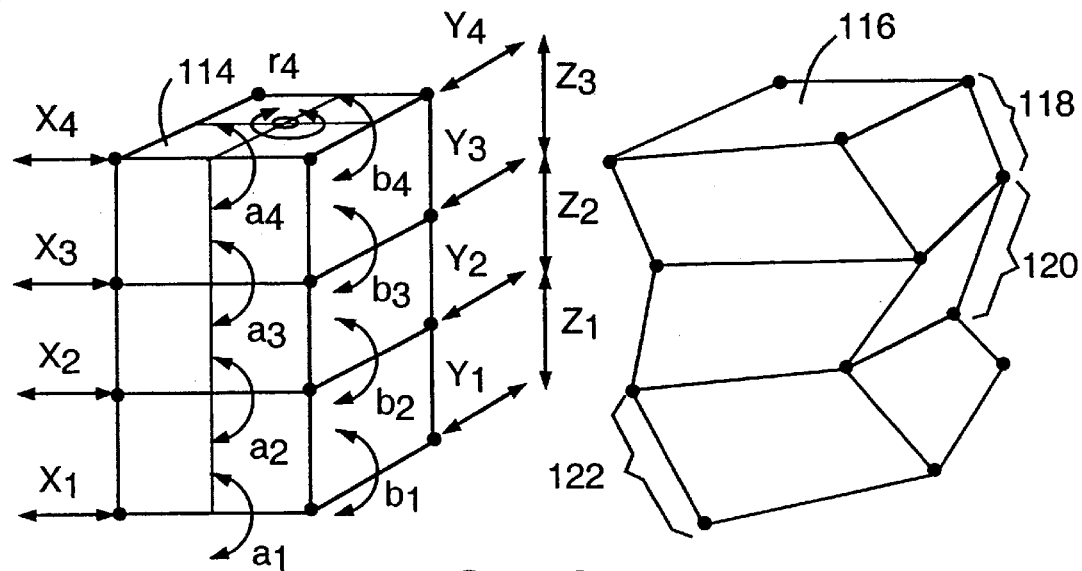
FIG. 9A shows free-form deformation parameters and lattices deformed according to the contour of the patient's bone.

In one embodiment, the 3D geometry reconstructor module 42 creates a 3D lattice 114 in which the template bone 112 from FIG. 8 is embedded. A free-form deformation process is applied to this 3D lattice 114 in order to optimally match with the contour of the patient's bone. For the sake of simplicity, a few of the free-form deformation (FFD) parameters are shown in FIG. 9A and identified as $a_i$, $b_i$, and $r_i$ (where i=1 to 4) in the x-y-z coordinate system for each parallelpiped (118, 120 and 122) in the 3D lattice 114. It may be desirable to have the 3D lattice 114 watertight in the sense that there may not be any gap and overlap between the faces of each constituent parallelpiped (118, 120 and 122) so as not to adversely affect a physical mockup made with a rapid prototyping process. In one embodiment, Sederberg and Parry's technique (hereafter "Parry's technique") may be used to reconstruct three-dimensional geometric model of the patient's bone. A detailed description of Parry's technique may be found in T. W. Sederberg and S. R. Parry, "Free Form Deformation of Solid Geometric Models," presented at SIGGRAPH '86 Proceedings, Dallas, Tex. (1986), which is incorporated herein by reference in its entirety.

Figure 12:
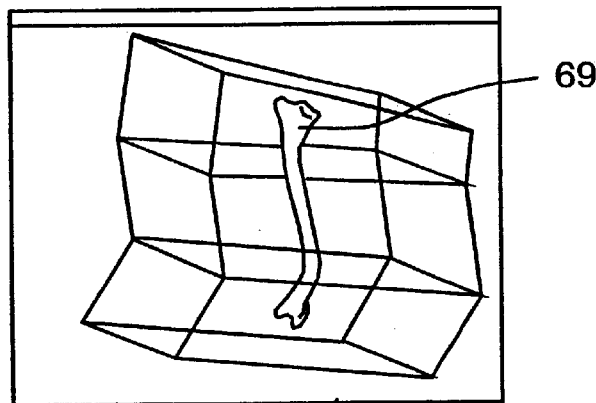
FIG. 12 depicts the deformed 3D geometric model and the deformed lattice for the patient's bone.

It is stated in A. H. Barr (hereafter "Bar"), "Global and Local Deformations of Solid Primitives," Computer Graphics, vol. 18, pp. 21–30 (1984), which is incorporated herein by reference in its entirety, that "Deformations allow the user to treat a solid as if it were constructed from a special type of topological putty or clay which may be bent, twisted, tapered, compressed, expanded, and otherwise transformed repeatedly into a final shape." Barr use a set of hierarchical transformations for deforming an object. This technique includes stretching, bending, twisting, and taper operators. However, Parry's technique deforms the space (e.g., the parallelpiped 3D lattice 114 in FIG. 9A) in which the object is embedded (as shown in FIG. 12). On the other hand, Coquillart's Extended Free-Form Deformation (EFFD) technique changes the shape of an existing surface either by bending the sure along an arbitrarily shaped curve or by adding randomly shaped bumps to the surface using non-parallelpiped type 3D lattices as discussed in S. Coquillart, "Extended Free-Form Deformation: A Sculpturing Tool for 3D Geometric Modeling," Computer Graphics, vol. 24, pp. 187–196 (1990) and in S. Coquillart, "Extended Free-Form Deformation: A Sculpturing Tool for 3D Geometric Modeling," INRIA, Recherche, France 1250 (June 1990), both of these documents are incorporated herein by reference in their entireties.

Here, Parry's FFD technique is applied to a new area of application, i.e., three-dimensional shape reconstruction from two-dimensional images, instead of to the traditional application domains of geometric modeling and animation. Additionally, hierarchical and recursive refinement is applied to the control grid of FFD to adjust the deformation resolution. Hierarchical refinement may be necessary because of the unique nature of the shape reconstruction problem, i.e., lack of a priori knowledge of the complexity or severity of the deformation, The basic idea of Parry's technique is that instead of deforming the object (here, the 3D template bone) directly, the object is embedded in a rectangular space that is deformed (as illustrated by FIG. 12). One physical and intuitive analogy of FFD is that a flexible object may be visualized as being "molded" in a clear plastic block and the whole block is deformed by stretching, twisting, squeezing, etc. As the plastic block is deformed, the object trapped inside the block is also deformed accordingly. Parry's technique uses the following single Bezier hyperpatch to perform this deformation:

$$q(u, v, w) = \sum_{i=0}^{n} \sum_{j=0}^{n} \sum_{k=0}^{n} P_{ijk} B_i(u) B_j(v) B_k(w), \qquad (1)$$

$$0 \le u \le 1, 0 \le v \le 1, 0 \le w \le 1$$

where u, v, and w are parameter values that specify the location of an original point in the control block space, q(u, v, w) specifies the location of the point after the deformation, $P_{ijk}$ specifies points that define a control lattice, and $B_i(u)$, $B_j(v)$, and $B_k(w)$ are the Bernstein polynomials of degree n, for example:

$$B_i(u) = \frac{n!}{i!(n-i)!} u^i (1-u)^{n-1} \qquad (2)$$

In equation (2), a linear version of FFD as a unit deformation block (i.e., n=1) may be used. This is the simplest deformation function, and there are only eight control points used to define a control block for deformation—these eight points define eight corner points of a deformation block (e.g., as shown by the corner points of each parallelpiped in the 3D lattice 114 in FIG. 9A). The variation of a deformation with a linear function is limited compared to a higher order function, but a linear function may be preferable because the complexity of the deformation of a bone is unknown a priori. It may also be desirable to increase the resolution of a deformation as needed by using adaptive refinement of the control block.

Figure 9B:
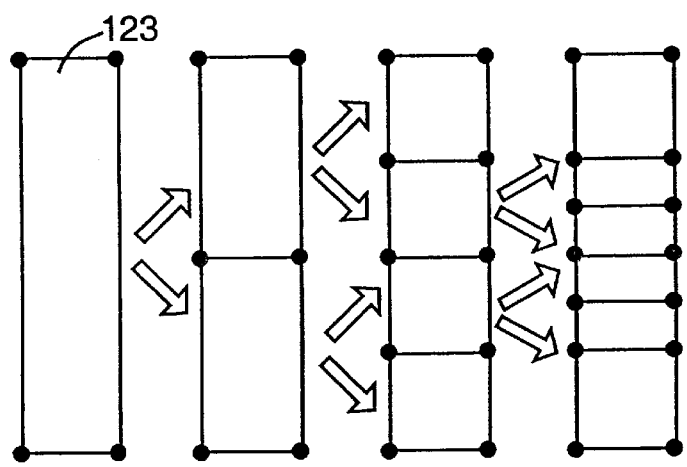
FIG. 9B illustrates a binary tree subdivision process on a control block.
Figure 9B:
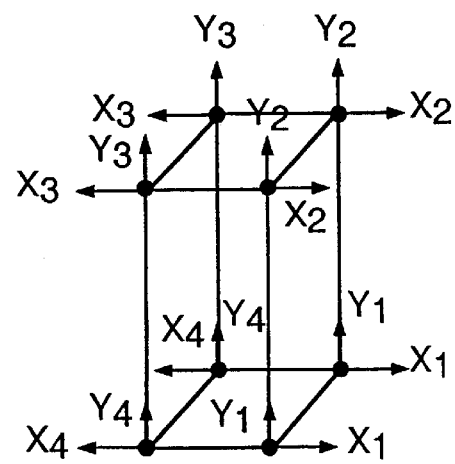

The adaptive refinement may be performed by using a hierarchical, recursive binary tree subdivision of the control block 123 as shown in FIG. 9B. A binary tree subdivision may be preferable rather than a more standard spatial subdivision of octree subdivision, because of the cylindrical or rim-type shape of the target bones (i.e., bones to be operated on) of a human patient. Octree may be a better choice when the target bone shape is not cylindrical. Furthermore, the extension from a binary subdivision to an octree subdivision may be straightforward.

Parry's technique calculates the deformed position $X_{ffd}$ of an arbitrary point X, which has (s, t, u) coordinates in the system given by the following equation:

$$X = X_o + sS + tT + uU \qquad (3)$$

The (s, i, u) coordinates are computed from the following equations:

$$s = \frac{T \times U \cdot (X - X_o)}{T \times U.S} \qquad (4)$$

$$t = \frac{S \times U \cdot (X - X_o)}{S \times U.T} \qquad (5)$$

$$u = \frac{S \times T \cdot (X - X_o)}{S \times T.U} \qquad (6)$$

A grid of the control points, $P_{ijk}$ in equation (7) is imposed on each parallelpiped (118, 120 and 122). This forms l+1 planes in the S direction, m+1 planes in the T direction, and n+1 planes in the U direction.

$$P_{ijk} = X_0 + \frac{i}{l} S + \frac{j}{m} T + \frac{k}{n} U \qquad (7)$$

The deformation is then specified by moving the $P_{ijk}$ from heir undisplaced, lattical positions according to the following equation:

$$X_{ffd} = \qquad (8)$$

$$\sum_{i=0}^{l} \binom{l}{i} (1-s)^{l-i} s^i \left[ \sum_{j=0}^{m} \binom{m}{j} (1-t)^{m-j} t^j \left[ \sum_{k=0}^{n} \binom{n}{k} (1-u)^{n-k} u^k P_{ijk} \right] \right]$$

A sequential quadratic programming (SQP) algorithm may then be used to compute free form deformation (FFD) parameters ($a_i$, $b_i$ and $r_i$ in FIG. 9A) that minimize the error between the X-ray image and the deformed bone image. Because the 3D geometry reconstructor module 42 creates three connected parallelpipeds (118, 120 and 122 in FIG. 9A), there are a total of eight parameters subject to optimization. More accuracy (i.e., minimization of error) may be achieved with increasing the number of parallelpiped lattices and also by increasing the number of FFD parameters. Before calculating the error, module A 42 may shrink the template bone data and the X-ray image data into a unit cube for convenient computation. The objective function of this minimization problem can be defined as follows:

$$\sum |P_n - Q_n(a_1, a_2, \ldots)| \qquad (9)$$

where $P_n$ represents points on the boundary of an X-ray image; $Q_n$ represents points on the deformed bone template; and $a_1$, $a_2$, etc. represent all deformation parameters (i.e., $a_i$, $b_i$ and $r_i$ in FIG. 9A). If there is no error between the X-ray image under consideration and the deformed bone image, and if the X-ray image is perfectly oriented, then the objective function in equation (9) above becomes zero.

Steps 95–102 in FIG. 5 depict the process of optimizing the FFD parameters and, hence, minimizing the error (in equation (9)) between a corresponding 2D X-ray image (e.g., the lateral view 65 or the AP view 66 or any other available view) and the appropriate view of the 3D template bone geometry 112 projected onto that X-ray image. Module A 42 projects (at step 95) the appropriate view of the 3D template bone geometry 112 onto the corresponding 2D X-ray image (e.g., views 65 or 66 in FIG. 4) and calculates the matching error (at step 96) between the projection and the X-ray image. Based on the error calculation, module A 42 attempts to optimize the FFD parameters at steps 98 and 100. The optimized values for the FFD parameters may then be used to generate the deformed polygonal mesh 116. At step 102, the 3D template bone model 112 is updated (i.e., deformed) with the new deformed polygonal mesh 116 taking into account the new deformation parameters.

The process outlined by steps 84–102 is continued for each new X-ray image (e.g., for the lateral view 65 as well as for the AP view 66 in FIG. 4) as indicated by the decision block 104. The process terminates at step 106 and the 3D geometry reconstructor module 42 outputs the final 3D bone geometry data (block 44 in FIGS. 3 and 4) in the form of a 3D deformed bone model 69 for the patient's bone 63. The optimized values of FFD parameters obtained for a specific 3D template bone corresponding to a given bone contour (e.g., the patient's bone 63) may be stored in the deformation mode database 54 for future reference as well as to facilitate 3D viewing. The 3D solid bone model 69 may then be viewed by the surgeon at the remote site 32 for further surgical planning as depicted by block 68 in FIG. 3.

Figure 13A:
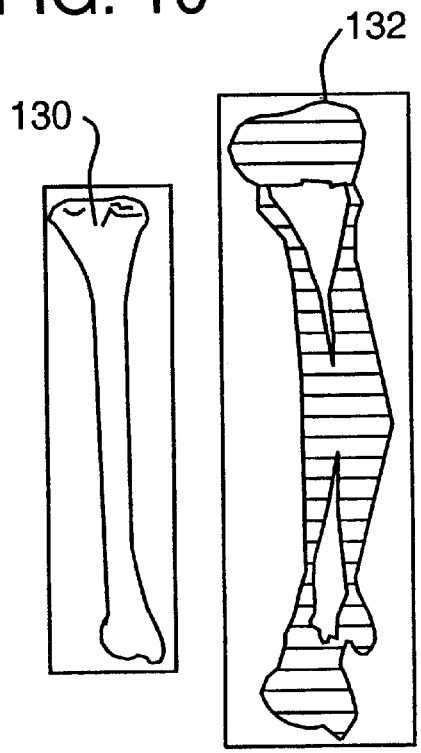
FIG. 13A depicts the initial error between an X-ray image and a deformed template bone generated using a three-cell lattice.
Figure 13B:
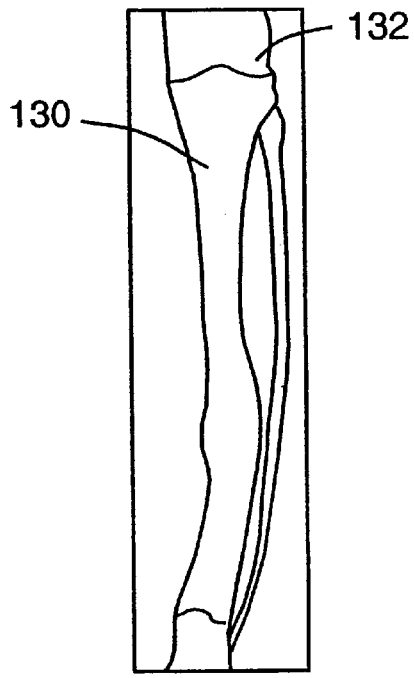
FIG. 13B depicts the initial error between an X-ray image and a deformed template bone generated using an eight-cell lattice.
Figure 14A:
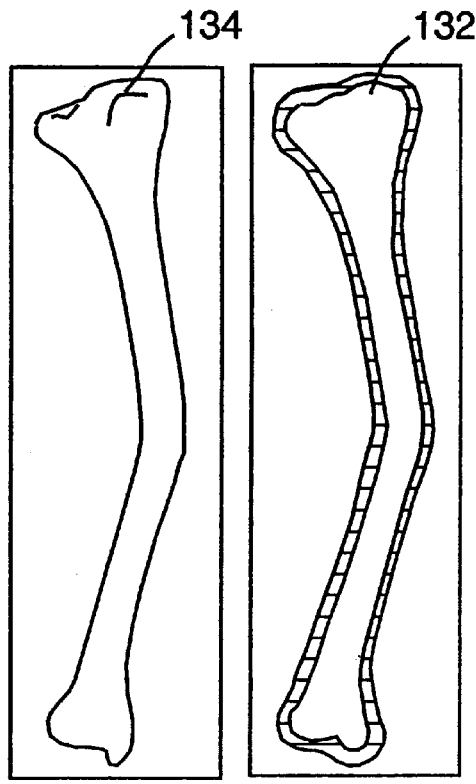
FIG. 14A depicts the final error between the X-ray image and the deformed template bone shown in FIG. 13A.
Figure 14B:
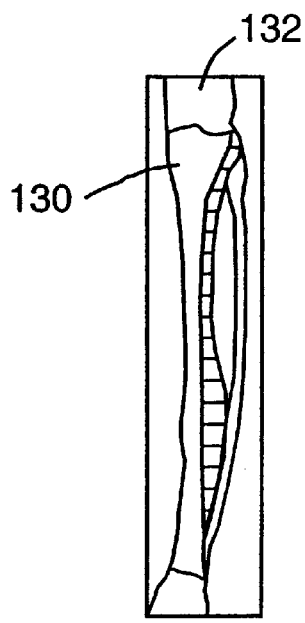
FIG. 14B depicts the final error between the X-ray image and the deformed template bone shown in FIG. 13B.

Certain of the steps discussed hereinbefore with reference to FIG. 5 are depicted in FIGS. 12, 13 and 14. FIG. 12 depicts the deformed 3D geometric model 69 and the deformed lattice 116 for the patient's bone 63. FIG. 13A depicts the initial error between an X-ray image 132 and a deformed template bone 130 generated using a lattice with three cells or three parallelpipeds (e.g., the lattice 114 in FIG. 9A). FIG. 13B, on the other hand, depicts the initial error between an X-ray image 132 and a deformed template bone 130 generated using a lattice with eight cells or eight parallelpipeds (e.g., the lattice resulting from the binary tree subdivision of the control block 123 in FIG. 9B). Due to significant errors in FIGS. 13A and 13B, the optimization process at steps 98, 100 (FIG. 5) may continue to minimize the projection error (i.e., to continue deforming the template bone 130). FIG. 14A depicts the final error between the X-ray image 132 and the deformed template bone 130 shown in FIG. 13A. In other words, FIG. 14A shows the final error in a deformation process that uses a lattice with free cells (e.g., the lattice 114 in FIG. 9A). On the other hand, FIG. 14B depicts the final error between the X-ray image 132 and the deformed template bone 130 shown in FIG. 13B. In other words, FIG. 14B shows the final error in a deformation process that uses a lattice with eight cells or eight parallelpipeds (e.g., the lattice resulting from the binary tree subdivision of the control block 123 in FIG. 9B). The eventually deformed template bone 134 may have bone geometry that closely resembles that of the patient's bone 63. The entire 3D bone model generation pass depicted in FIG. 5 may be implemented in any suitable programming language, such as, e.g., the C++ programming language, and may be executed on any suitable computer system, such as, e.g., a personal computer (PC), including the computer assisted orthopedic surgery planner computer 30. The final deformed bone geometry 69 may be displayed on the display screen 40 (FIG. 2) and may also be sent to the surgeon at the remote site 32 over the communication network 34 as discussed hereinbefore.

Figure 10:
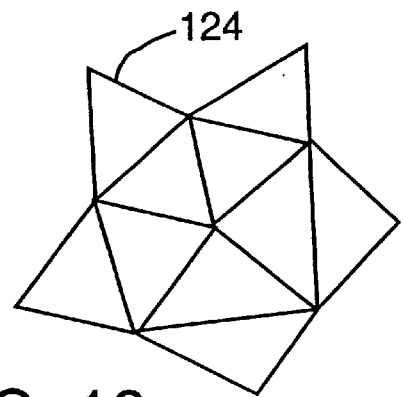
FIG. 10 illustrates a template triangular mesh in a physical-based approach to bone geometry reconstruction.

In an alternative embodiment, a physical-based approach may be used to create a 3D solid (or deformed) template bone model (i.e., the model 69 in FIG. 4) that may later be used by the surgeon at the remote site 32 for, e.g., mockup surgery practice. As part of the deformation process, first, a template polygonal mesh that represents a standard parametric geometry and topology of a bone is defined. The length and girth of the polygonal mesh is scaled for each patient based on the size of the corresponding 3D template bone model (e.g., the 3D template bone model 112 in FIG. 8). A model consisting of parametric surfaces, such as Bézier surfaces and non-uniform rational B-spline (NURBS) surfaces may provide increased resolution FIG. 10 illustrates a template triangular mesh 124 in a physical-based approach to bone geometry reconstruction. The contours of the 3D template bone model 112 (FIG. 8) may be visualized as being composed of the triangular mesh 124.

Figure 11:
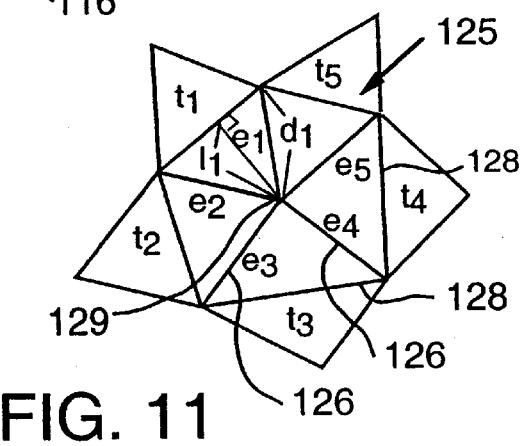
FIG. 11 illustrates extension springs and torsion springs defined over a deformable triangular mesh model.

Thereafter, the template polygonal mesh (here, the triangular mesh 124) is converted into a deformable model consisting of a system of stretched springs and bent springs. FIG. 11 illustrates extension springs ($e_i$) and torsion springs ($t_i$) defined over a deformable triangular mesh model 125. Then, multiple X-ray images (e.g., images 65 and 66 in FIG. 4) are used to generate force constraints that deform and resize the deformable model 125 until the projections of the deformed bore model conform to the input X-ray images as shown and discussed hereinbefore with reference to FIGS. 13 and 14. A standard library of image processing software routines that filter, threshold and perform edge detection may be used to extract (for comparison with the projections of the deformed bone model) the two dimensional bone boundaries from the X-ray images as discussed hereinbefore.

Referring now to FIG. 11, the extension springs ($e_i$) are defined over the edges 126 and the torsion springs ($t_i$) are defined over the edges 128 for a node 129 under consideration. It is assumed that the original length of an extension spring is given by an edge (e.g., the edge 126) of the template polygon mesh (here, the triangular mesh 125) so that the tensile force is proportional to the elongation of that edge. The spring constant of an extension spring may be denoted as 'k'. It is also assumed that the original angle of a torsion spring is given by the template mesh (here, the mesh 125) so that the torque exerted by the torsion spring is computed based on the angular displacement The spring constant of a torsion spring may be denoted as '$\beta_i$'.

The total force 'f' exerted on a node (e.g., the center node 129) is calculated by summing: (1) the tensile forces '$f_{g_i}$' applied by all the extension springs attached to the node, and (2) the forces '$f_{t_i}$' applied by all the torsion springs surrounding the node 129. In the deformable triangular mesh model 125, five extension springs $e_i$(i=1 to 5) and five torsion springs $t_i$(i=1 to 5) exert forces on the center node 129. The total force 'f' is thus calculated as the summation of the forces from all the springs as given by the following equation:

$$f = \sum_{i=1}^{N} f_{e_i} + \sum_{i=1}^{N} f_{j_i} \quad (10)$$
$$= \sum_{j=1}^{N} k d_i + \sum_{i=1}^{N} \frac{\beta_i \theta_i}{l_i}$$

where N is the number of edges attached to the node (here, the center node 129). Thus, N is equal to the number of triangles surrounding the node. Furthermore, in equation (10), $d_i$ is the length of the extension spring $e_i$, $\theta_i$ is the angle between the normal vectors of He two triangles that share the torsion spring $t_i$ as a common edge, and $l_i$ is the perpendicular distance from the node (here, the center node 129) to the torsion spring $t_i$.

By defining the equation of motion of this spring system and by numerically integrating the equation of motion, an equilibrium configuration of the spring system that minimizes the potential energy of the system can be given by the following equation:

$$U = \sum_{\substack{all \\ nodes}} \left( \sum_{i=1}^{N} \frac{1}{2} k d_i^2 + \sum_{i=1}^{N} \frac{1}{2} \beta_i \theta_i^2 \right) \quad (11)$$

Thus, each triangle in the deformable triangular mesh 125 may get deformed according to the force constraints generated by the resulting mismatch (at steps 95,96 in FIG. 5) when the image of the 3D template bone geometry 112 (FIG. 8) is projected onto a corresponding 2D X-ray image (e.g., the lateral view 65, the AP view 66, etc.). The deformation of the triangular mesh 125 may continue until the matching error is minimized as indicated by steps 96, 98,100 and 102. Upon minimization of the matching error, an equilibrium condition may get established as given by equation (11). The equilibrium process outlined above for the triangular mesh spring model of FIGS. 10 and 11 may be repeated for each X-ray image of the patient's bone 63 as denoted by the decision step 104 in FIG. 5.

Figure 15:
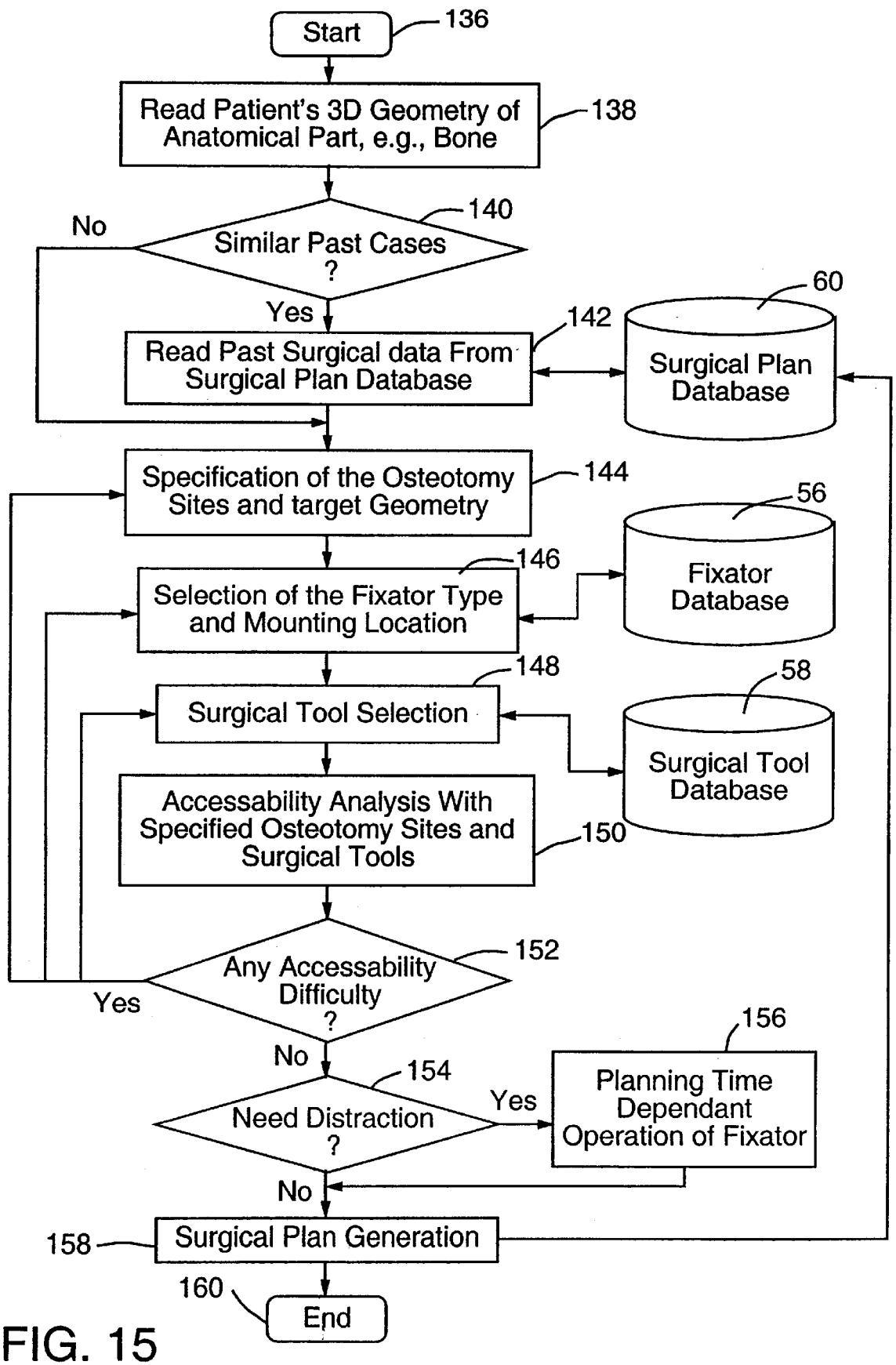
FIG. 15 is an exemplary flowchart depicting operational steps performed by the surgical planner/simulator module of the computer assisted orthopedic surgery planner software according to the present invention.

FIG. 15 is an exemplary flowchart depicting operational steps performed by the surgical planner/simulator module (or module B) 46 of the computer assisted orthopedic surgery planner software according to the present invention. Module B 46 assists a surgeon in making a detailed surgical plan by utilizing accurate 3D bone models (generated by module A 42) and realistic 3D computer graphics and animation. Upon initial execution (at step 136), the planner module 46 reads or takes as an input (at step 138) the 3D geometry of the patient's anatomical part (here, the patient's bone 63). This 3D geometry may have been generated earlier by the 3D geometry reconstructor module 42 as discuss hereinbefore with reference to FIGS. 5–14. Thereafter, the surgeon viewing the 3D bone model 69 may determine (at step 140) whether any similar past case exists where the bone treated had similar 3D geometry as the current patient's bone 63. The surgeon may make the decision either upon manual review of the patient's 3D bone geometry 69 or using the surgical plan database 58 or any similar data storage. Alternatively, module B 46 may perform similar decision-making based on a comparison with the data stored in the surgical plan database 60.

Figure 1:
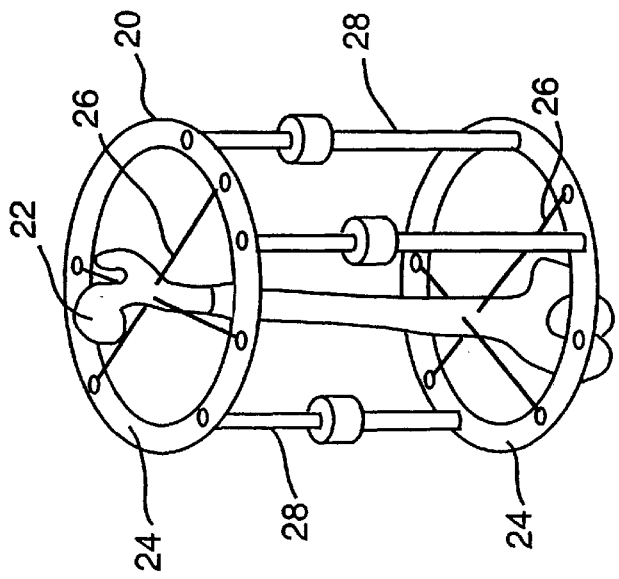
FIG. 1 illustrates a prior art Ilizarov fixator attached to a bone.

If there is a past case that involves a bone having similar 3D geometry as the current patient's bone 63, then the surgeon may instruct (at step 142) module B 46 to read the surgical data associated with the past case from the surgical plan database 60. Alternatively, upon finding a matching or similar past case, module B 46 may automatically perform a search of the surgical plan database 60 to retrieve and send pertinent past surgical data to the surgeon at the remote site 32 so that the surgeon may determine whether to follow the steps performed earlier in another case or to alter or improve the earlier executed surgical plan. Whether there is a past similar case or not, the surgical planner module 46 generates a specification of the osteotomy site(s) and of the target geometry (e.g., the mounting arrangement 75 in FIG. 4) at step 144. Thereafter, at step 146, the planner module 46 may access the fixator database 56 to select the appropriate fixator type (e.g., the Ilizarov fixator 20 of FIG. 1 or the Taylor Spatial Frame 162 of FIG. 16). Further, during step 146, the planner module 46 may also generate information about the least intrusive mounting location for the fixator selected.

Module B (i.e., the planner module 46) may further continue the optimum and most efficient surgical plan generation process by selecting (at step 148), from the surgical tool database 58, appropriate surgical tools that may be needed to perform osteotomy or bone distraction on the patient's bone 63. Module B 46 may take into account the 3D geometry of the template bone model 69 generated by module A 42 to determine the most useful set of tools for the desired surgical Ore. The surgical planner module 46 then performs an analysis (at step 150) of how easily accessible the osteotomy site (specified earlier at step 144) is with the current selection of surgical tools (at step 148). The surgical planner module 46 may analyze (at the decisional step 152) its accessibility determination at step 150 based on, for example, an earlier input by the surgeon as to the kind of surgery to be performed on the patient's bone 63 and also based on the contour data available from the 3D template bone geometry generated by module A 42. If the planner module 46 determines any difficulty (e.g., difficulty in mounting the fixator or difficulty in accessing the osteotomy site, etc.) with the currently determined accessibility approach, then the planner module 46 may reevaluate its earlier determinations as shown by the iteration performed at step 152.

Upon determining a viable (i.e., easily accessible and least intrusive) surgical plan for the patient's bone 63, the planner module 46 may further prepare a time-line for the bone distraction operation (at step 156) based on a decision at step 154. The surgeon at the remote site 32 may specify prior to executing the computer assisted orthopedic surgery planner software whether bone distraction needs to be performed and whether the surgeon would like to have a computer-based time-line for the distraction process (including such steps as fixator mounting, daily adjustment of struts and final removal of the fixator). Finally, at step 158, the planner module 46 generates an optimum surgical plan 48 (FIGS. 3 and 4) for the patients bone 63 based on available bone geometry and other surgical data. Prior to ending at step 160, module B 46 may store the recommended surgical plan in the surgical plan database 60 for future reference (e.g., for case comparison in a future case) and may also send the plan 48 to the surgeon at the remote site 32 via the communication network 34. In one embodiment, the surgical plan 48 may include a report documenting: (1) animation of the bone distraction process, (2) type and size of the fixator frame and its struts, (3) a suggested fixator frame mounting plan, (4) the osteotomy/coricotomy site location, (5) locations of fixator pins, and (6) the day-by-day length adjustment schedule for each fixator strut The surgeon at the remote site 32 may view the suggested surgery plan 48 received from the computer assisted orthopedic surgery planner computer 30 as depicted by block 70 in FIG. 3. The realistic 3D computer graphics and animation contained in the simulated surgery plan create a CAD (computer aided design) environment that can help a surgeon better understand the three-dimensional positional relationships between the bone, the fixator, the osteotomy/coricotomy site, and the fixator pins. Because the surgeon would be able to create and verify the operation plan using easy-to-understand three-dimensional views, a more precise plan could be made in a shorter period of time. In one embodiment, the three-dimensional graphics for the surgical plan 48 may be generated using the OpenGL (open graphics library) software interface developed by Silicon Graphics, Inc., of Mountainview, Calif., USA. The OpenGL graphics software interface may be implemented on a conventional PC (personal computer) platform to show animations of the bone distraction process.

The 3D simulation of the proposed surgical plan is depicted as the initial simulation 72 in FIG. 4. The computer-assisted surgical simulation 72 depicts the 3D template bone geometry 69 for the patient's bone 63 with a Taylor Spatial Frame 73 mounted thereon according to the specifications computed by module B 46. The final location and orientation of the fixator frame 73 on the 3D solid bone model 69 is depicted by the simulated target position 75 in FIG. 4. Thus, the initial operational position 72 and the final or desired target position 75 are simulated by the surgical planner module 46 to guide the surgeon during the actual surgery.

Figure 16:
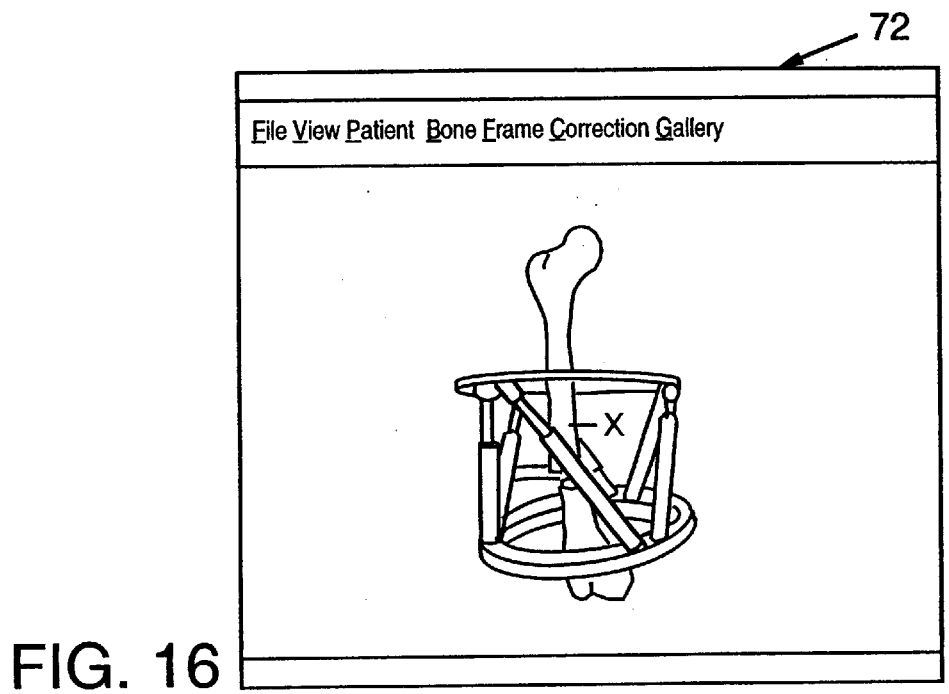
FIG. 16 is an exemplary three-dimensional surgical simulation on a computer screen depicting a fixator, a bone model and the coordinate axes used to identify the bone's deformity and the osteotomy site.

FIG. 16 also shows the initial three-dimensional surgical simulation 72 on a computer screen depicting the fixator 73, the 3D solid bone model 69 and the coordinate axes used to identify the bone's deformity and the osteotomy site. The location of the suggested cutting of the bone for the bone distraction is also visible in the 3D simulated model 72 in FIG. 16.

Figure 17:
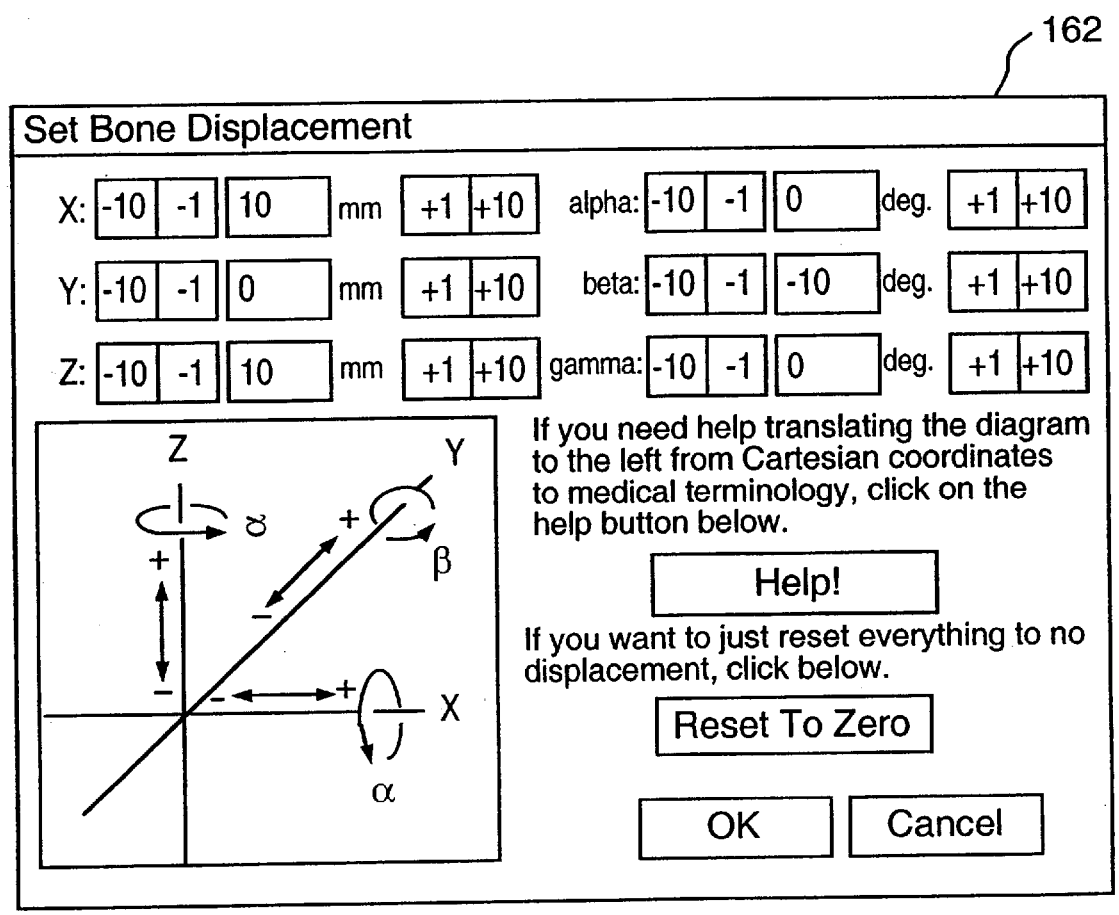
FIG. 17 shows an example of a graphical user interface screen that allows a user to manipulate the 3D simulation shown in FIGS. 4 and 16.

FIG. 17 shows an example of a graphical user interface (GUI) screen 162 that allows a user (e.g., a surgeon) to manipulate the 3D simulations 72 or 75 shown in FIGS. 4 and 16. Thus, the surgeon at the remote site 32 may manipulate the 3D simulated models 72 or 75 with a pointing device (e.g., a computer mouse) and through the Microsoft Windows® dialog box (or GUI) 162 on the screen of the computer where the surgeon is viewing the 3D models. Using the dialog box or the GUI 162 the surgeon may correct the stress-tension for the struts in the fixator frame 73 and view the simulated results prior to actually attempting the surgery.

The surgeon may then perform the surgery as suggested by the surgical plan generated by the computer assisted orthopedic surgery planner software module B 46. X-ray imaging is again used to measure all the relative positions after the fixator frame (e.g., the Taylor Spatial Frame 73) has been actually mounted (at block 74 in FIG. 3) and after the osteotomy/coricotomy has been made by the surgeon. A computer-aided surgery module may measure the actual positions of the bone deformity relative to the attached fixator and coricotomy, and the surgeon at the remote site 32 may feedback or input the positional data generated by such measurement into the computer assisted orthopedic surgery planner software for final determination of the distraction schedule based on the actual surgical data. The feedback data from the surgery may be sent to the computer assisted orthopedic surgery planner computer 30 over the communication network 34 as shown by the post-surgery X-ray images data output from block 76 in FIG. 3.

Figure 18:
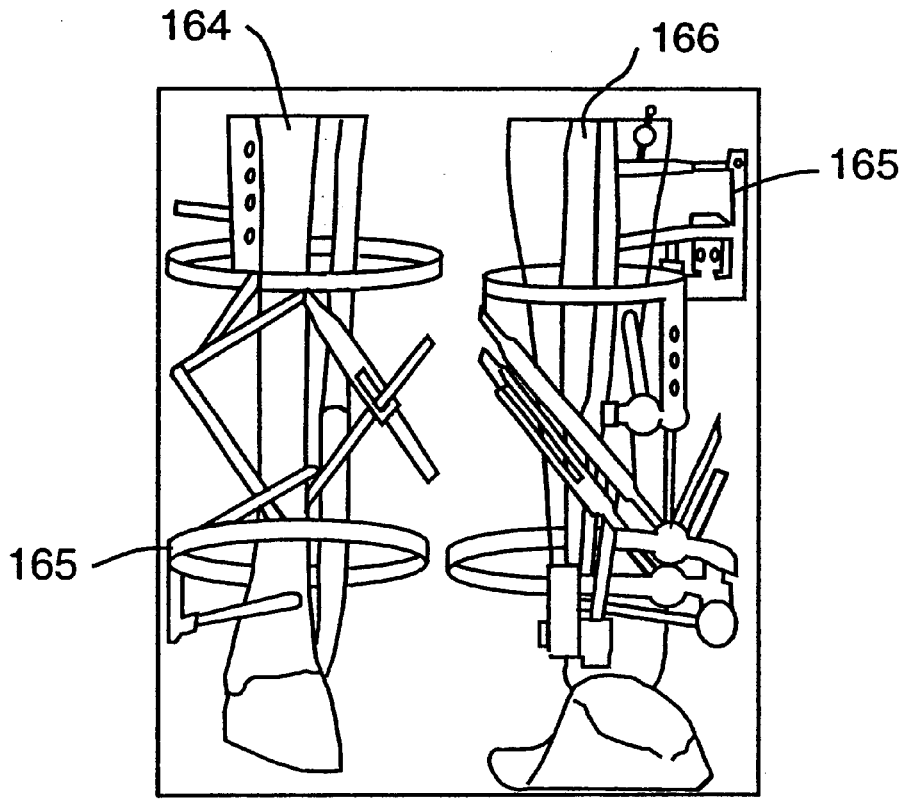
FIG. 18 depicts post-surgery X-ray images of a patient's bone along with the X-ray image of the fixator mounted thereon.

FIG. 18 depicts post-surgery X-ray images (164, 166) of a patient's bone along with the X-ray image (165) of the fixator mounted thereon. The X-ray image 164 may correspond to the post-surgery lateral view 78 and the X-ray image 166 may correspond to the post-surgery lateral view 80 shown in FIG. 4. The digitized versions of these post-surgery X-ray images 164, 166 may be sent to the computer assisted orthopedic surgery planner software as denoted by block 76 in FIG. 3. Upon receipt of the post-surgery X-ray data, the computer assisted orthopedic surgery planner software module B 46 may act on the data to identify deviation, if any, between the suggested surgical plan data and the actual surgery data. Thereafter, module B 46 may revise the earlier specified distraction trajectory (at step 156 in FIG. 15) to assure a correct kinematic solution in view of any discrepancy between the pre-surgery plan data and the post-surgery data. Module B 46 may still optimize the distraction plan even if the fixator is not mounted exactly as pre-surgically planned.

Figure 19:
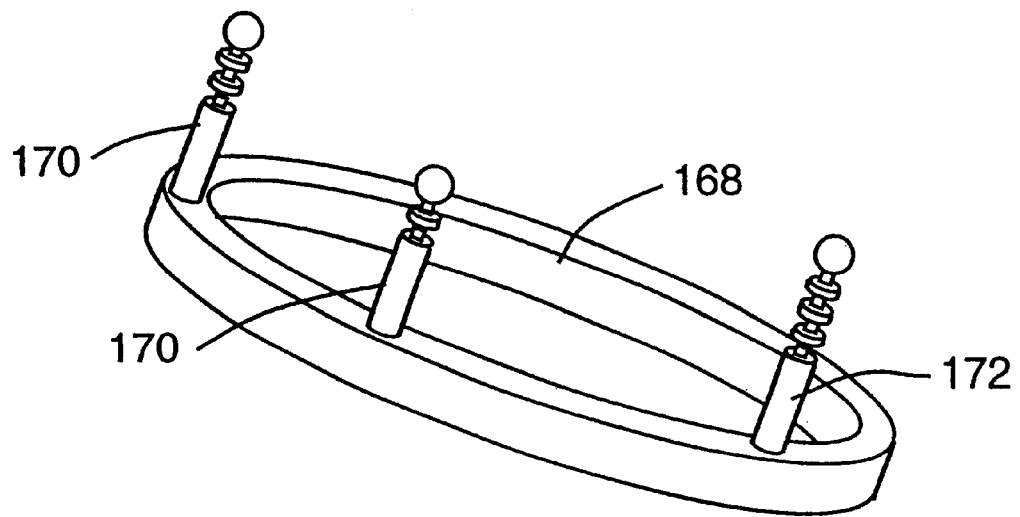
FIG. 19 illustrates an exemplary fixator ring incorporating easily identifiable and detachable visual targets.

In one embodiment, to facilitate imaging and measurement of the fixator's position, a modified design for the fixator ring may be used. FIG. 19 illustrates an exemplary fixator ring 168 incorporating easily identifiable and detachable visual targets 170. The fixator ring 168 in FIG. 19 may be used as part of a ring for the Ilizarov fixator 20 (FIG. 1) or the Taylor Spatial Frame 73 (FIGS. 4 and 16). For example, the modified fixator ring 168 may replace the ring 24 in the Ilizarov fixator 20 shown in FIG. 1. The geometrical feature or targets 170 may be easily identifiable in computerized X-ray images. In the embodiment shown in FIG. 19, three posts (or targets or markers) 170 are attached to the ring 168 with each post having a unique geometry (here, the number of groves on the post) to identify the marker's 170 position in the X-ray image of the corresponding fixator. More or less than three posts may also be utilized. Furthermore, one or more posts may include a target sphere 172 at their open ends as shown. Thus, the surgeon may easily identify the fixator as well as the orientation of the fixator on the patient's bone.

After acquiring the X-ray image (e.g., a post-surgery X-ray image) and after performing automatic filtering, thresholding and edge detection on the X-ray image, the digitized X-ray image may be displayed on a window on a computer screen (e.g., the display screen 40 in FIG. 2 or a display screen of a computer at the remote site 32). The location of geometrical targets 170 may be done by a simple and reliable user-interactive mode. For example, the computer assisted orthopedic surgery planner computer 30 or the surgeon's computer at the remote site 32 may be configured to prompt the surgeon attending the computer to identify each target post 170 by moving the computer's cursor (or pointing with a computer mouse) over the approximate location of the marker's sphere 172 and then clicking to select. The computer may be configured (e.g., with a search software) to automatically search a bounded area to localize the sphere 172 and measure its relative position. This process may be done in both the AP and the lateral views. Similarly, the osteotomy/coricotomy may be located by prompting the surgeon to draw a line with the cursor (or with a computer mouse) over the osteotomy's location in the X-ray images. Because the position of each sphere 172 relative to the ring 168 that it is attached to would be known a priori, the positions and orientations of all rings on a fixator frame could thus be measured relative to the osteotomy/coricotomy. The targets 170, 172 could be removed from the fixator rings 168 before discharging the patient.

The foregoing describes exemplary embodiments of a computer assisted orthopedic surgery planner software according to the present invention. It is noted that although the discussion hereinabove focuses on the use of the computer assisted orthopedic surgery planner software for a patient's bone, the software may also be used for surgical planning and 3D modeling of any other anatomical part of the patient's body. Some of the major areas of applications of the computer assisted orthopedic surgery planner software of the present invention include: (1) Bone deformity correction including (i) osteotomy planning, simulation and assistance for, e.g., long bone deformities, complex foot deformities, (ii) acute fracture stabilization and secondary alignment in multiple trauma, and (iii) distraction osteogenesis case planning, simulation and assistance for, e.g., congenital and acquired deformities; (2) Maxillofascial as well as plastic reconstructive surgery; (3) Telemedicine or web-based surgical planning for physicians at distant locations; (4) Aide in the design of custom prosthetic implants; (5) Axial realignment when doing cartilage joint resurfacing; and (6) Creation of anatomical models for education of students and surgeons (e.g., for mock practice of surgical techniques).

The computer assisted orthopedic surgery planner software according to the present invention facilitates generation and simulation of accurate 3D models of a patient's anatomical part, e.g., a bone. Furthermore, in the complex area of bone distraction surgery, the computer assisted orthopedic surgery planner software makes accurate surgical plans based solely on a number of two-dimensional renderings or X-ray images of bone geometry. The software takes into account the complex and inherently three-dimensional nature of bone deformities as well as of fixator geometry when preparing a simulation of the proposed surgical plan prior to actual surgery. Complexities involved in accessing the target positions of the osteotome and fixator pins surrounding the operated bone are substantially reduced with the help of CAD (computer aided design) tools and 3D simulation of surgical environment. Three-dimensional modeling allows for an accurate mounting of a fixator frame on the patient's bone according to a pre-surgical plan.

An Internet-based bone distraction planning service may be offered on a subscription-basis or on a per-surgery basis to surgeons located at remote places where computer assisted orthopedic surgery planner software may not be directly available. An expert surgeon may operate the service provider's computer assisted orthopedic surgery planner terminal to devise a surgical plan and distraction schedule for the remotely-located surgeon based on the X-ray image(s) data and other specific requests received from the remote surgeon over the Internet.

As noted hereinbefore, there are fewer than 1% of orthopedic surgeons who practice bone distraction. Furthermore, the external fixation with distraction currently takes an average of twelve to sixteen weeks at a cost of $1800 per week. However, even more time is required if the fixator was not initially properly mounted as often occurs in complicated cases. In these cases, the distraction schedule must be changed or the fixator must be reinstalled. The risk of major complications, including bone infection or fixation to bone failure rises exponentially when treatment times are extended. Complications and reinstallation of the fixator can require additional surgery costing $5000 to $10,000 and further extending the duration of fixation.

With the computer-aided pre-operative planning and frame application and adjustment methods described hereinabove, the duration of fixation (of a fixator frame) may be reduced by an average of four to six weeks. Additionally, by lowering the frequency of prolonged fixations, the cost savings may be approximately $9000 per patient. Shortening of the treatment time and reduction of complications may lead to better surgical results and higher patient satisfaction. The use of the computer assisted orthopedic surgery planner software of the present invention (e.g., in the lnternet-based bone distraction surgery planning service) may make the frame fixation and bone distraction processes physician-friendly by simplifying fixation, decreasing preoperative planning time, and reducing the chances of complications through realistic 3D simulations and bone models.

While several embodiments of the invention have been described, it should be apparent, however, that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

What is claimed is:

1. A method of generating a computer-based 3D (three-dimensional) model for a patient's anatomical part comprising:

defining a 3D template model for the patient's anatomical part;

receiving a plurality of 2D (two-dimensional) X-ray images of the patient's anatomical part;

extracting 2D fiducial geometry of the patient's anatomical part from each of said plurality of 2D X-ray images; and deforming the 3D template model using the 2D fiducial geometry of the patient's anatomical part so as to minimize an error between contours of the patient's anatomical part and those of the deformed 3D template model.

2. The method of claim 1, wherein debug the 3D template model includes selecting the 3D template model from a set of 3D template models stored in an electronic database.

3. The method of claim 1, wherein receiving the plurality of 2D X-ray images includes receiving said each of the plurality of 2D X-ray images in a digitized form.

4. The method of claim 1, wherein receiving the plurality of 2D X-ray images includes:

generating the plurality of 2D X-ray images of the patient's anatomical part; and digitizing said each of the plurality of 2D X-ray images.

5. The method of claim 1, wherein the patient's anatomical part is a bone.

6. The method of claim 1, wherein extracting 2D fiducial geometry includes detecting surface contours of the patient's anatomical part from said each of the plurality of 2D X-ray images.

7. The method of claim 1, wherein deforming the 3D template model includes:

identifying the 2D fiducial geometry of the patient's anatomical part on the 3D template model therefor;

embedding the 3D template model into a 3D lattice; and deforming the 3D lattice until a projection error between one of the plurality of 2D X-ray images and a corresponding view of the 3D template model projected thereon is minimized.

8. The method of claim 7, wherein deforming the 3D lattice includes:

computing a plurality of free form deformation (FFD) parameters for the 3D lattice; and optimizing values for the plurality of FFD parameters so as to minimize the error between the contours of the patient's anatomical part and those of the deformed 3D template model.

9. The method of claim 7, wherein the 3D lattice is constituted of a plurality of parallelpipeds.

10. The method of claim 1, wherein said each of said plurality of 2D X-ray images is contained in a plane that is orthogonal to the planes containing the remainder of said plurality of 2D X-ray images.

11. A method of creating a 3D (three-dimensional) model of a bone, comprising:
   extracting a bone contour from a plurality of 2D(two-dimensional) X-ray images;
   identifying the bone contour on a 3D template bone model;
   adjusting a size and position of the template bone model based on the bone contour; and,
   minimizing the differences between the adjusted template bone model and the X-ray images.

12. The method of claim 11, further comprising creating a surgical plan based on the template bone model.

13. The method of claim 11, wherein minimizing differences includes minimizing differences based on a plurality of free form deformation parameters.

14. The method of claim 11, wherein adjusting a size and position of the template bone model includes adjusting size and position of the template bone model until they are optimum.

15. The method of claim 11, further comprising accepting the plurality of X-ray images in digital format.

16. The method of claims 11, further comprising accepting a position of a camera.

17. A system, comprising:
   a 3D (three-dimensional) template geometry database having stored therein at least one 3D template bone model; and,
   a 3D geometry reconstructor module;
   wherein the reconstructor module creates a 3D model of a bone by:
      extracting a bone contour from a plurality of 2D (two-dimensional) X-ray images;
      identifying the bone contour on a 3D template bone model;
      adjusting a size and position of the template bone model based on the bone contour; and,
      minimizing the differences between the adjusted template bone model and the X-ray images.

18. A system of claim 17, wherein the geometry reconstructor module is further for accepting the plurality of X-ray images in digital format.

19. A system of claim 17, further comprising a deformation mode database.

20. A 3D (three dimensional) geometry reconstructor, comprising:
   means for extracting a bone contour from a plurality of 2D (two-dimensional) X-ray images;
   means for identifying the bone contour on a 3D template bone model;
   means for adjusting a size and position of the template bone model based on the bone contour; and,
   means for minimizing the differences between the adjusted template bone model and the X-ray images.

* * * * *